(12) United States Patent
Adams et al.

(10) Patent No.: US 7,059,331 B2
(45) Date of Patent: *Jun. 13, 2006

(54) METHOD AND DEVICE FOR FULL THICKNESS RESECTIONING OF AN ORGAN

(75) Inventors: Ronald D. Adams, Holliston, MA (US); Roy H. Sullivan, III, Millville, MA (US); George A. Nunez, Miami, FL (US); Lauren O. Main, Somerset, MI (US); Peter K. Kratsch, Sunrise, FL (US); Jurgen A. Kortenbach, Miami Springs, FL (US); Matt Solar, Cooper City, FL (US); Gerhard F. Buess, Tübingen-Bebenhausen (DE); Marc O. Schurr, Tübingen (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

This patent is subject to a terminal disclaimer.

(21) Appl. No.: 10/251,192

(22) Filed: Sep. 19, 2002

(65) Prior Publication Data

US 2003/0019905 A1  Jan. 30, 2003

Related U.S. Application Data

(60) Division of application No. 10/055,306, filed on Jan. 23, 2002, now Pat. No. 6,478,210, which is a continuation of application No. 09/813,944, filed on Mar. 22, 2001, now Pat. No. 6,343,731, which is a continuation of application No. 09/694,894, filed on Oct. 25, 2000, now Pat. No. 6,241,140.

(51) Int. Cl.
*A61B 19/00* (2006.01)

(52) U.S. Cl. .................................. 128/898; 227/180.1
(58) Field of Classification Search ................ 128/898; 227/176.1, 179.1, 180.1
See application file for complete search history.

(56) References Cited

U.S. PATENT DOCUMENTS

| 5,088,979 A | * | 2/1992 | Filipi et al. ..................... 604/26 |
| 5,355,897 A | * | 10/1994 | Pietrafitta et al. ............ 128/898 |
| 5,395,030 A | * | 3/1995 | Kuramoto et al. ......... 227/179.1 |
| 5,403,326 A | * | 4/1995 | Harrison et al. ............. 606/139 |

(Continued)

*Primary Examiner*—Gary Jackson
(74) *Attorney, Agent, or Firm*—Fay Kaplun & Marcin, LLP

(57) ABSTRACT

A full-thickness resection system comprises a flexible endoscope and a stapling mechanism, wherein the endoscope is slidably received through at least a portion of the stapling mechanism. The stapling mechanism comprises an anvil and a stapling head mounted to the anvil so that the anvil and the stapling head are moveable with respect to one another between a tissue receiving position and a stapling position and wherein a gap formed between the stapling head and the anvil is larger in the tissue receiving position than it is in the stapling position. A position adjusting mechanism is provided for moving the anvil and the stapling head between the tissue receiving and stapling positions and a staple firing mechanism sequentially fires a plurality of staples from the stapling head across the gap against the anvil and through any tissue received in the gap and a knife cuts a portion of tissue received within the gap. A control unit which remains outside the body is coupled to the stapling mechanism for controlling operation of the position adjusting mechanism and the staple firing mechanism.

1 Claim, 29 Drawing Sheets

U.S. PATENT DOCUMENTS

| | | | |
|---|---|---|---|
| 6,117,148 A * | 9/2000 | Ravo et al. | 606/153 |
| 6,126,058 A * | 10/2000 | Adams et al. | 227/180.1 |
| 6,544,271 B1 * | 4/2003 | Adams et al. | 606/139 |
| 6,592,596 B1 * | 7/2003 | Geitz | 606/139 |
| 6,663,639 B1 * | 12/2003 | Laufer et al. | 606/139 |
| 6,736,828 B1 * | 5/2004 | Adams et al. | 606/213 |

* cited by examiner

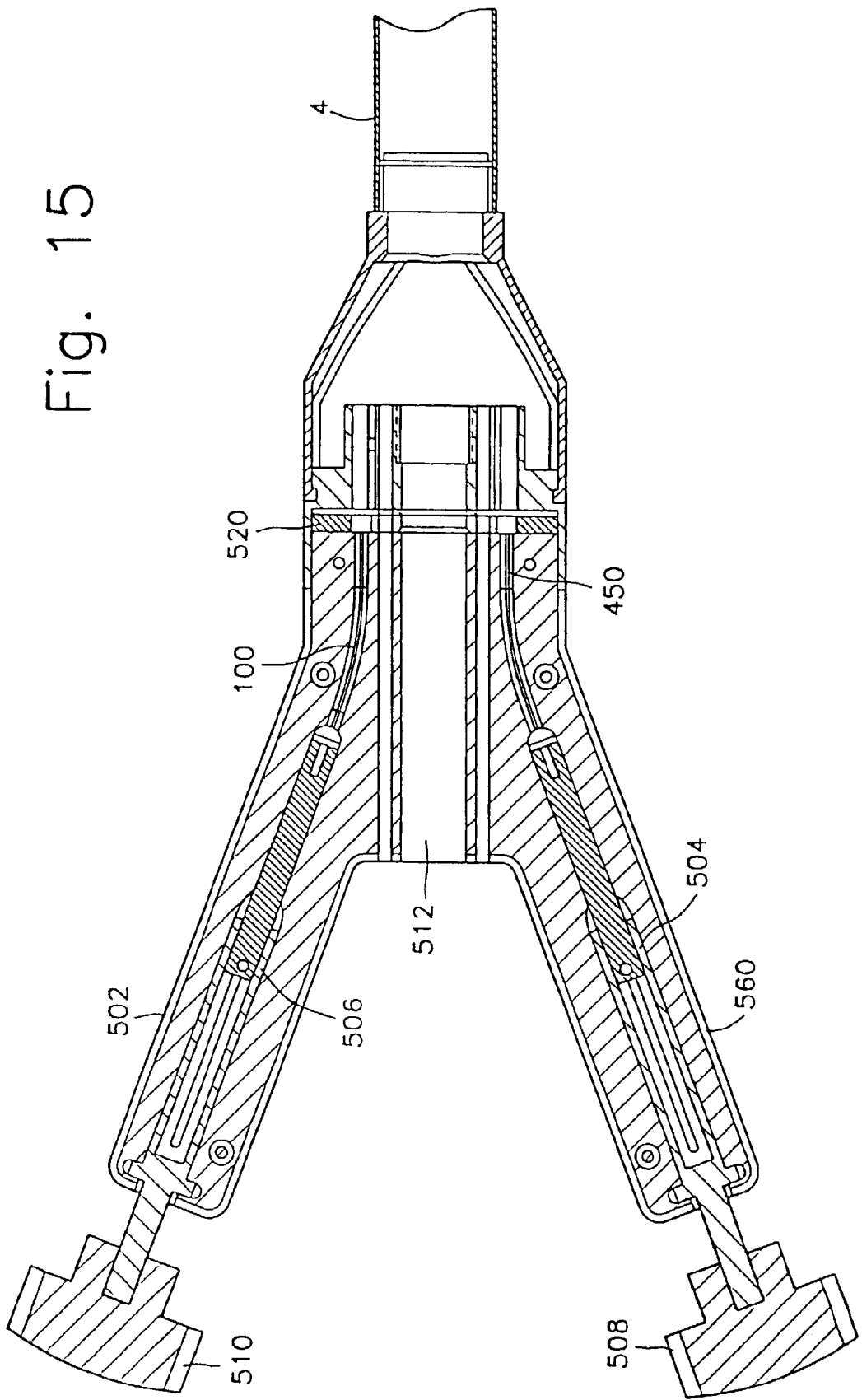

METHOD AND DEVICE FOR FULL THICKNESS RESECTIONING OF AN ORGAN

This application is a Division of prior U.S. patent application Ser. No. 10/055,306 filed Jan. 23, 2002 now U.S. Pat. No. 6,478,210 entitled "Method and Device for Full Thickness Resectioning of an Organ" which is a Continuation of U.S. Ser. No. 09/813,944 filed Mar. 22, 2001 now U.S. Pat. No. 6,343,731 entitled "Method and Device for Full Thickness Resectioning of an Organ" which is a Continuation of U.S. Ser. No. 09/694,894 filed Oct. 25, 2000 now U.S. Pat. No. 6,241,140 entitled "Method and Device for Full Thickness Resectioning of an Organ". All applications are expressly incorporated herein, in their entirety, by reference.

FIELD OF THE INVENTION

The present invention relates to full thickness resection devices for performing localized resections of lesions in tubular organs, particularly the colon.

BACKGROUND INFORMATION

A resection procedure involves excising a portion of an organ, approximating the surrounding tissue together to close up the hole created by the excision, and removing the excess tissue. Various conventional devices and procedures are available for resectioning lesions in tubular organs.

For example, several known resection devices and procedures requires at least one incision in an area near the portion of the organ to be excised for access to the lesion or treatment site (because, for example, the resectioning device may lack steering and/or viewing capabilities). Thus, the incision is required to allow the physician to access the organ section to be excised and guide the device to that section. Alternatively, when the organ section to be excised is beyond the reach of the surgical device, or the surgical device is not flexible enough to wind through the organ to the site to be excised, an incision will be required to position the device for the procedure. Of course, these incisions are painful and may involve a partial or entire loss of mobility while recuperating from the incision, in addition to recovering from the tubular resectioning procedure itself. In addition, the time required to recover from such a procedure is often longer than for procedures which do not require incisions.

One type of conventional resection procedure utilizes a circular stapling instrument in which a tubular section of a tubular organ is excised, resulting in the tubular organ being separated into a first segment and a second segment. The end sections of the first and second segments are then individually tied in a purse-string fashion, approximated, stapled, and the "purse-stringed" end sections are then cut off. In this full circle resectioning procedure, at least one separate invasive incision must be made near the section to be excised in order to cut and individually tie the separate end sections of the organ. Also, a separate incision is necessary to place one part of the resectioning device in the first segment and a corresponding second part of the device in the second segment so that the device can then bring the first and second segments together to re-attach the organ sections back together. A first of these separate parts may generally include a staple firing mechanism while the second part includes an anvil for forming the staples. Thus, this type of resectioning procedure involves the drawbacks mentioned above in regard to procedures requiring invasive incisions. In addition, the separation of the organ into two segments creates the risk of spillage of non-sterile bowel contents into the sterile body cavity, which can cause severe infection and possibly death.

An alternative resectioning device includes a stapling and cutting assembly on a shaft which can be bent or formed into a desired shape and then inserted into a patient's body cavity. Once the shaft has been bent into the desired shape, the rigidity of the shaft ensures that that shape is maintained throughout the operation. This arrangement limits the effective operating range of the device as the bending of the shaft into the desired shape before insertion and the rigidity of the shaft once bent require the physician to ascertain the location of the organ section to be removed before insertion, and deform the shaft accordingly. Furthermore, the rigidity of the shaft makes it difficult to reach remote areas in the organ—particularly those areas which must be reached by a winding and/or circuitous route (e.g., sigmoid colon). Thus, an incision may be required near the organ section to be excised in order to position the device at the organ section to be excised.

SUMMARY OF THE INVENTION

The present invention is directed to a full-thickness resection system comprising a flexible endoscope and a stapling mechanism, wherein the endoscope is slidably received through at least a portion of the stapling mechanism. The stapling mechanism includes an anvil and a stapling head mounted to the anvil so that the anvil and the stapling head are moveable with respect to one another between a tissue receiving position and a stapling position and wherein a gap formed between the stapling head and the anvil is larger in the tissue receiving position than it is in the stapling position. A position adjusting mechanism is provided for moving the anvil and the stapling head between the tissue receiving and stapling positions and a staple firing mechanism sequentially fires a plurality of staples from the stapling head across the gap against the anvil and through any tissue received in the gap and a knife cuts a portion of tissue received within the gap. A control unit which remains outside the body is coupled to the stapling mechanism for controlling operation of the position adjusting mechanism and the staple firing mechanism.

BRIEF DESCRIPTION OF THE DRAWINGS

FIG. 10b shows a cut-away view of the wedge of FIG. 10a;

FIG. 10c shows a blade portion corresponding to the wedge of FIG. 10a;

FIG. 15 shows a control handle for use with the devices according to the present invention;

FIG. 19b shows a tissue blocker of the blade shield of FIG. 19a;

FIG. 19c shows a distal end of a proximal housing of the device of FIG. 19a.

DETAILED DESCRIPTION

Figure 1:
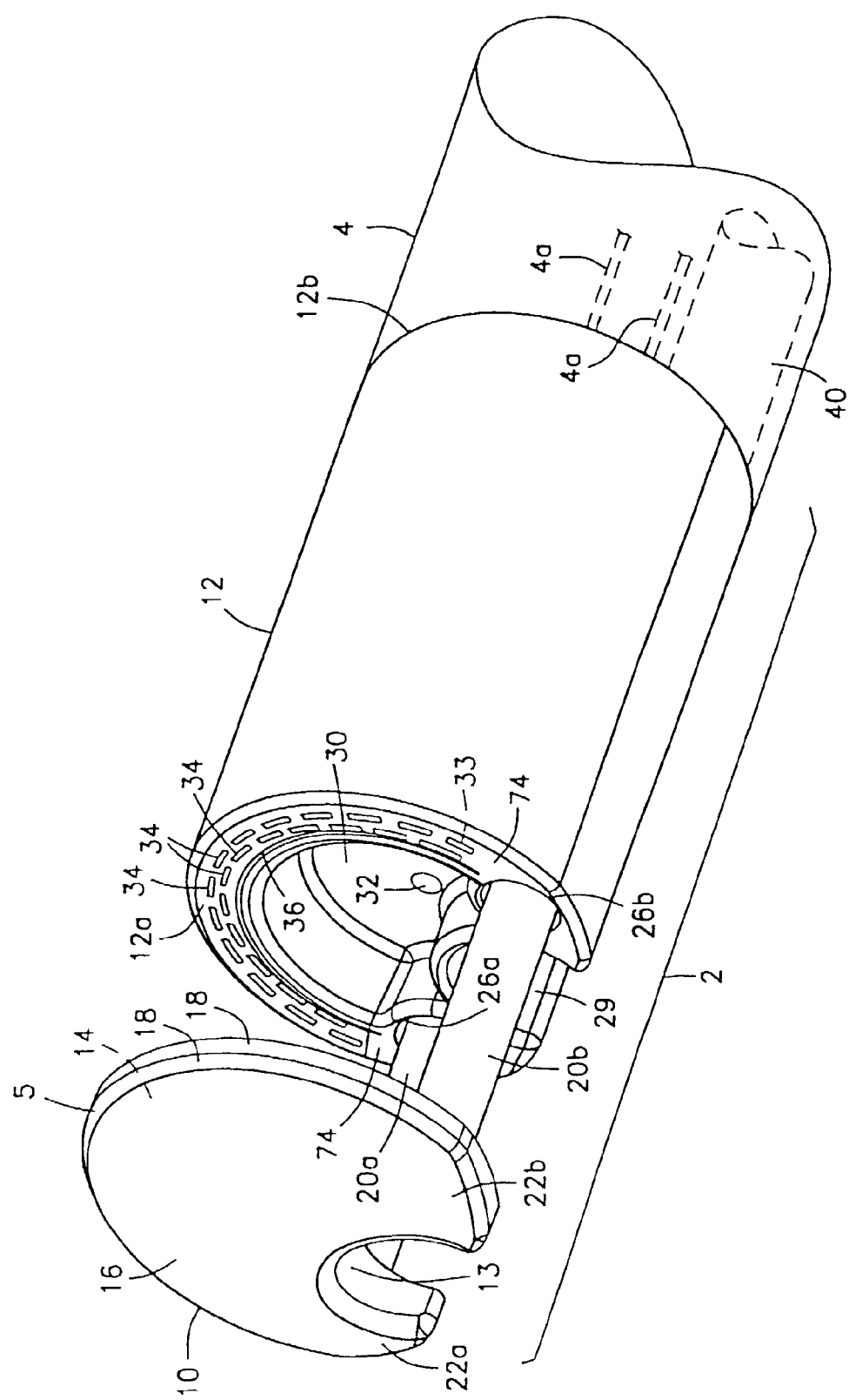
FIG. 1 shows a device according to a first embodiment of the present invention.
Figure 2:
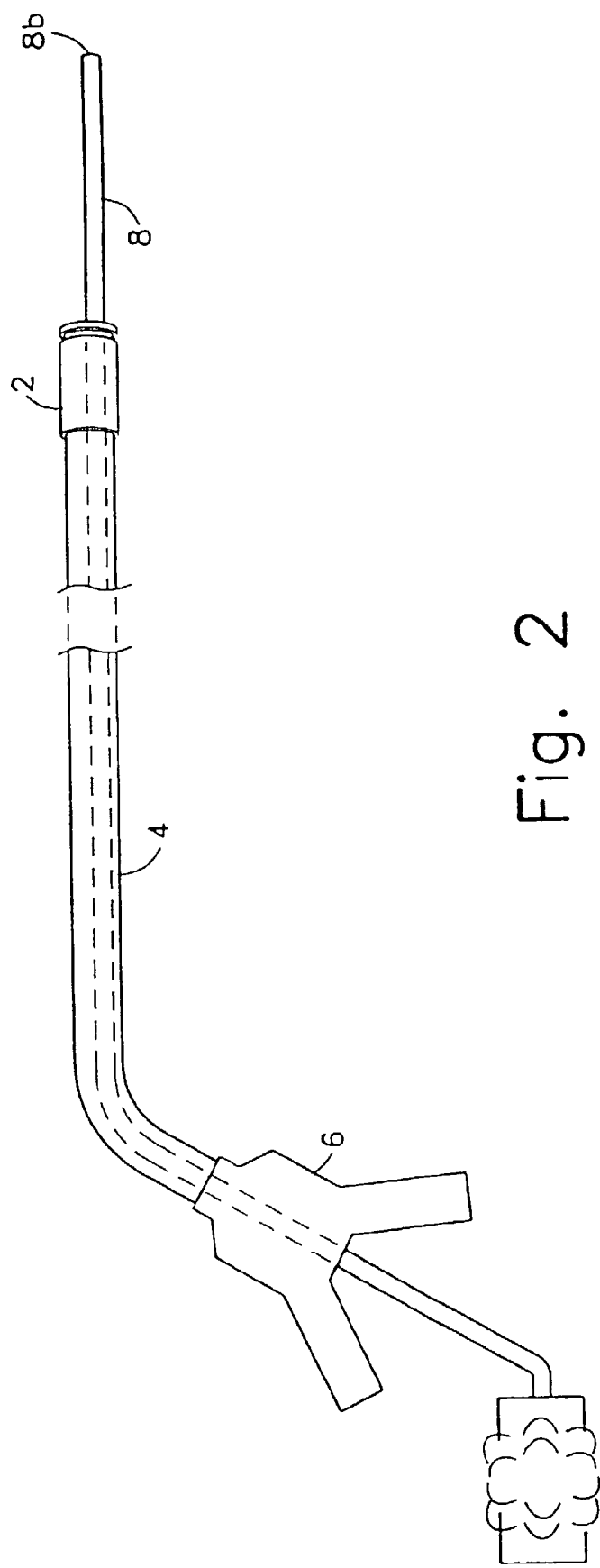
FIG. 2 shows the device of FIG. 1 mounted on a conventional endoscope.

As shown in FIGS. 1 and 2, an apparatus according to a first embodiment of the present invention comprises a working head assembly 2 which may preferably be connected to a distal end 4a of a sheath 4. The proximal end 4b of the sheath 4 may preferably be connected to a control handle 6.

In operation, the entire apparatus is mounted onto an endoscope 8 by passing the endoscope 8 through the control handle 6, the sheath 4, and the working head assembly 2, as shown in FIG. 2. The endoscope 8 is then inserted into a body orifice to locate a lesion in the tubular organ under visual observation (usually while insufflating the organ). Once the lesion has been located, the working head assembly 2 and the sheath 4 are slidably advanced along the endoscope 8 into the tubular organ until the working head assembly 2 is in a desired position adjacent to the lesion. Those skilled in the art will understand that in an alternative embodiment, the working head assembly 2 may also be detachably coupled to a distal end of the endoscope 8, and the entire arrangement may then be inserted into the body orifice under visual observation.

As shown in FIG. 1, the working head assembly 2 comprises an anvil member 10 coupled to a distal end 12a of a proximal housing 12. The anvil member 10 has a substantially crescent-shaped cross-section (i.e., the outer edge 18 of the anvil member 10 substantially forms a portion of a first circle with a second smaller circular cut-out 13 formed within the first circle) with a proximal face 14 and a smaller distal face 16. The cut-out 13 of the anvil member 10 is included to allow the endoscope 8 to be slid through the entire working head assembly 2 so that the endoscope 8 may be advanced into the body passage allowing the working head assembly 2 to later be advanced into the body to the lesion. In addition, the cut-out 13 also provides forward vision via the endoscope 8. Thus, any shape of the cut-out 13 may be selected which is large enough to accommodate the endoscope 8, with a larger cut-out providing a larger field of vision. An outer surface 18 of the anvil member 10 extends substantially parallel to a central axis of the working head assembly 2 while the proximal and distal faces 14, 18 of the anvil member 10 extend in planes substantially perpendicular to the central axis. The outer surface 18 is joined to the distal face 16 by a tapered portion 5.

Figure 3:
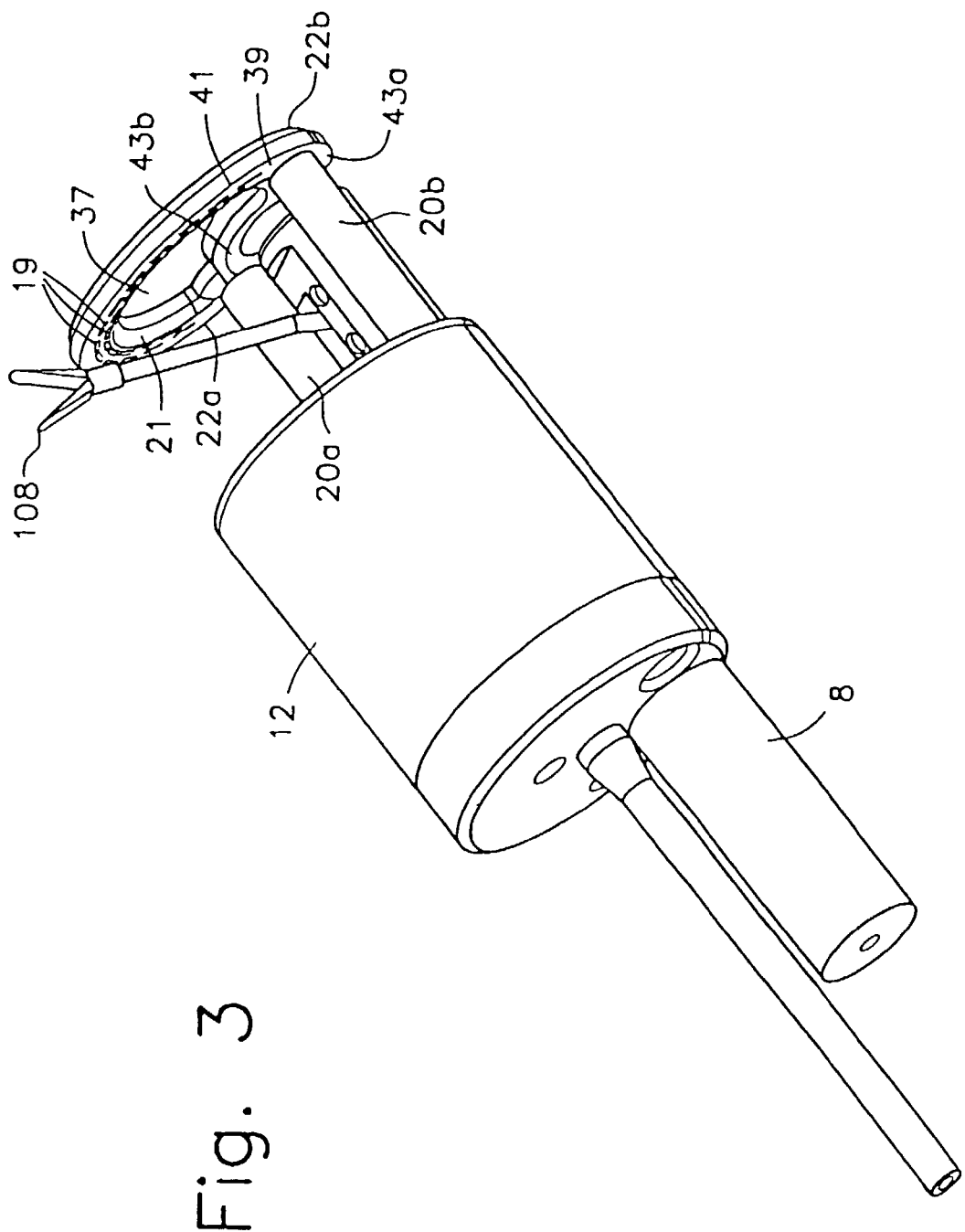
FIG. 3 shows the device of FIG. 1 with a grasper mechanism extending therefrom.

As shown in FIG. 3, the proximal face 14 of the anvil member 10 includes a first cavity 37 and a rim 41 encircling the first cavity 37. A plurality of staple-forming grooves 19 are arranged in two offset rows on the rim 41 of the anvil member 10 and a circular guiding slit 21 extends radially within the rows of grooves 19. The rim 41 protrudes from the remainder of the proximal face 14 so that a shallow cavity is formed on the proximal face 14.

Figure 3A:
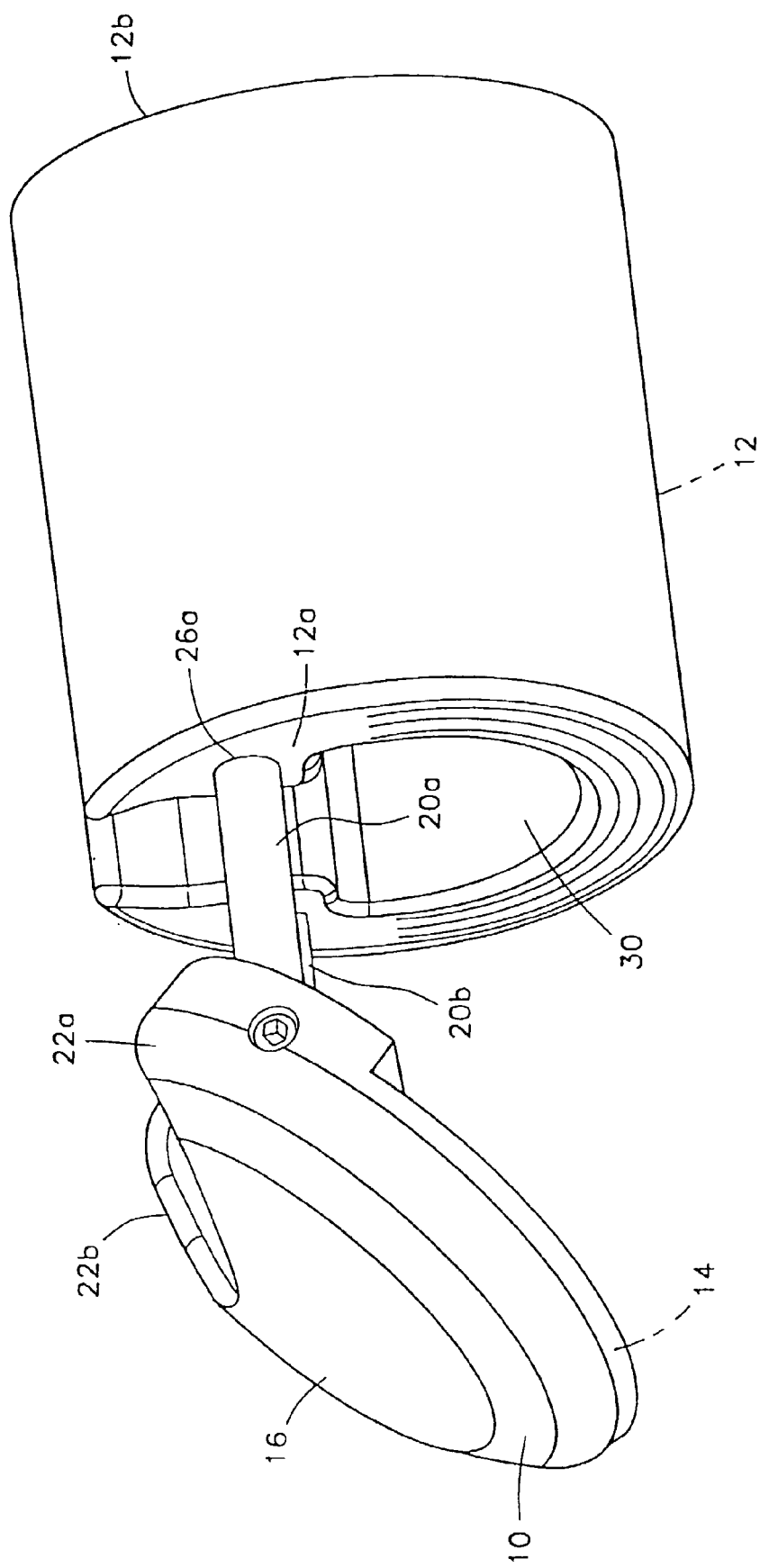

The anvil member 10 is coupled to the proximal housing 12 by means of two mounting shafts 20a and 20b, which may preferably be substantially cylindrical. Each mounting shaft 20a, 20b is coupled to the proximal face 14 of the anvil member 10 on a respective one of two horns 22a, 22b formed by the crescent-shaped anvil member 10. Although the anvil member 10 is shown fixedly coupled to the mounting shafts 20a, 20b, those skilled in the art will understand that the anvil member 10 may also be pivotally coupled to the mounting shafts 20a, 20b in order to provide a greater field of vision through the endoscope 8 as shown in FIG. 3a. In this pivoted-type arrangement, the anvil member 10 is angled in a first configuration so that the horns 22a, 22b are closer to the distal end 12a of the proximal housing than the rest of the anvil member 10. Then, as the anvil member 10 is drawn towards the distal end 12a of the proximal housing 12, the anvil member 10 would be pressed against the distal end 12a beginning with the horns 22a, 22b, which would cause the anvil member 10 to pivot until the proximal face 14 of the anvil member 10 is parallel to the distal end 12a.

As shown in FIG. 1, the mounting shafts 20a, 20b are slidably received in mounting holes 26a, 26b, which have a size and shape substantially corresponding to the size and shape of the mounting shafts 20a, 20b and which run axially through the proximal housing 12. The mounting shafts 20a, 20b are preferably movable axially proximally and distally within the mounting holes 26a, 26b between a proximal most position in which a tissue gripping gap of a first predetermined width is formed between the rim 41 and the distal end 12a of the proximal housing 12, and a distal most position in which a tissue receiving gap of a larger second predetermined width is formed between the rim 41 and the distal end 12a of the proximal housing 12. The second predetermined width should preferably be more than twice the thickness of a wall of the organ being resectioned so that a section of the tubular organ may be pulled into a resectioning position between the anvil member 10 and the proximal housing 12.

Figure 4:
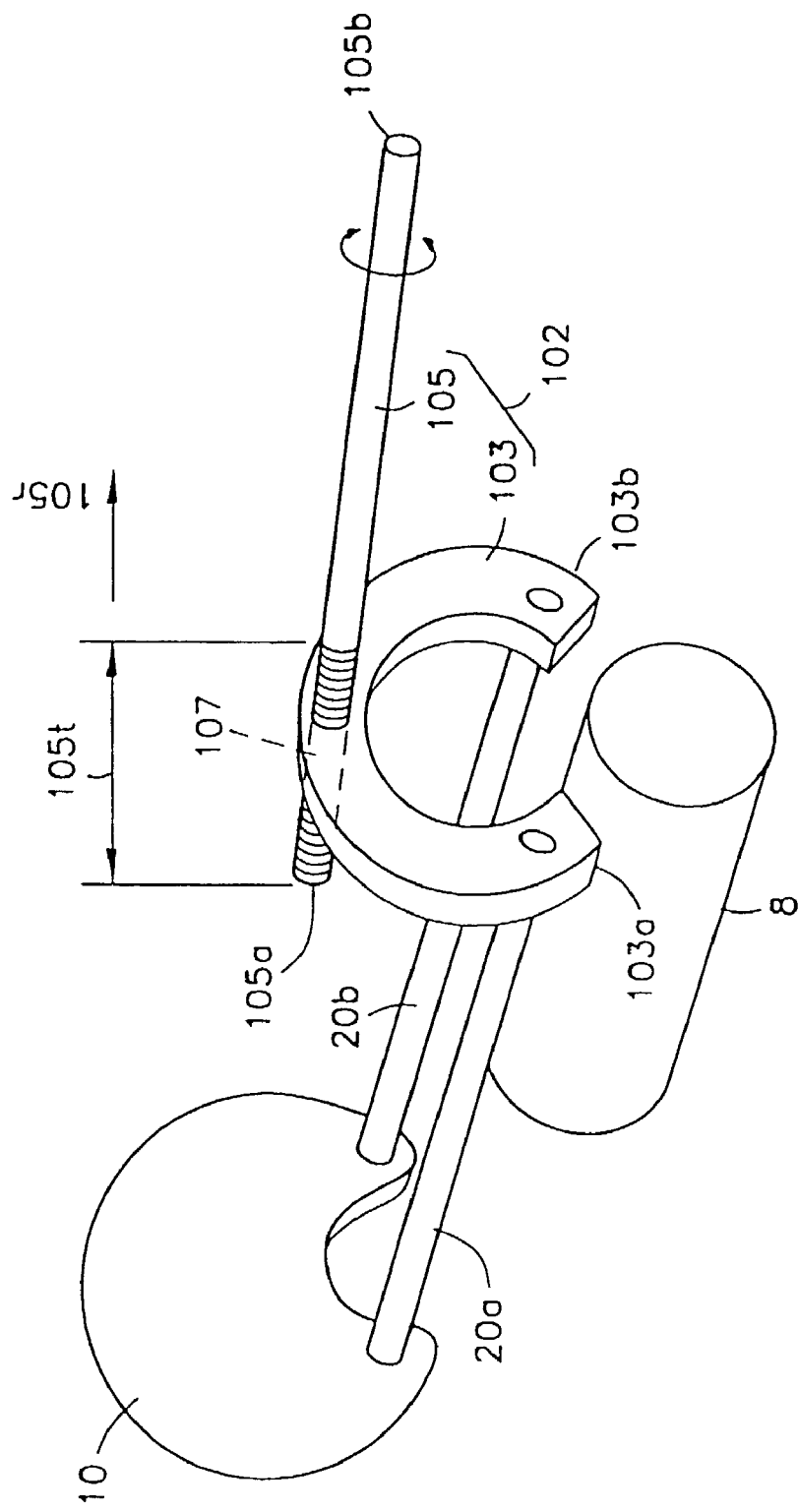
FIG. 4 shows a cutaway of the device of FIG. 1 showing a drive mechanism thereof.

As shown in FIG. 4, the proximal end of at least one of the mounting shafts 20a and 20b is coupled to a drive mechanism 102 provided within the proximal housing 12. In a preferred embodiment, the drive mechanism 102 is composed of a yoke 103 and a drive shaft 105. The yoke 103 is preferably slidably received within the proximal housing 12 for longitudinal movement along the axis of the proximal housing 12 so that, when the anvil member 10 is in the proximal most position, the yoke 103 is in a corresponding proximal most position and, when the anvil member is in the distal most position, the yoke 103 is in a corresponding distal most position.

The yoke 103 may preferably be substantially semicircular with a substantially rectangular cross-section. Although the semicircle formed by the yoke 103 in FIG. 4 forms substantially a quarter arc of a circle, the yoke 103 may form a larger semicircle based upon the interior accommodations of the proximal housing 12 and the position of the mounting shafts 20a, 20b. The mounting shaft 20a may preferably be coupled to the yoke 103 at a first end 103a of the yoke 103, and the mounting 20. shaft 20b may be coupled at a second end 103b of the yoke 103. A shaft hole 107, having a diameter substantially corresponding to a diameter of a complementarily threaded distal end 105a of the drive shaft 105, extends through the yoke 103 at a point substantially midway between the first end 103a and second end 103b. Thus, when the drive shaft 105 is rotated, the threaded distal end 105a engages the shaft hole 107 to move the yoke 103 proximally or distally (in dependence upon the direction of rotation of the drive shaft 105).

The distal end 105a of the drive shaft 105 should preferably be threaded over a first section 105t substantially corresponding in length to at least the distance between the proximal and distal most yoke positions, while a remainder portion 105r may have no threads thereon. The drive shaft 105 may have an increased cross-section in the areas immediately adjacent to the threaded first section 105t (proximally and/or distally of section 105t), thereby limiting the movement of the yoke 103 to the first section 105t. Those skilled in the art will understand that the drive shaft 105 is preferably rotatably mounted within the proximal housing 12 so that it may only rotated and may not move relative to the proximal housing 12. The drive shaft 105 preferably extends to a proximal end 105b which is coupled to a drive cable 100 which extends to the control handle 6 through the sheath 4. The drive cable 100 may preferably run axially along the peripheral interior of the sheath 4. Those skilled in the art will understand that the sheath 4 is preferably torsionally stiff to resist the torque forces from the drive cables rotating therein. However, the sheath 4 is longitudinally flexible to so that it may be slidably advanced along the endoscope 8, while minimizing interference with the operation of the endoscope 8 and trauma to surrounding tissue. The sheath 4 is preferably constructed similar to known endoscope insertion tubes, which are flexible yet allow the transfer of forces to swivel the distal end of the endoscope 8 in multiple directions nd the torqueable rotation of the endoscope.

Figure 8:
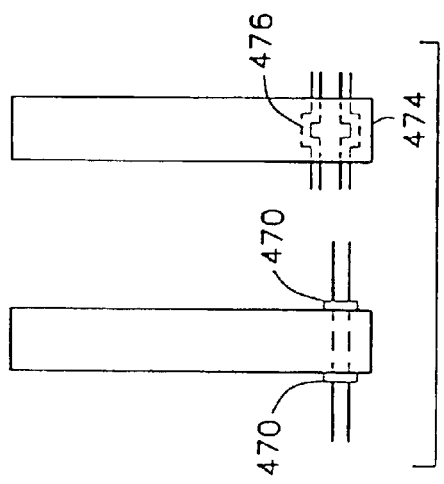
FIG. 8 shows a rear cover plate of the working head assembly of FIG. 7.

FIGS. 7–10 show a cutaway view of the working head assembly 2 in FIG. 1, in which the respective movements of the drive shaft 105 and the yoke 103 are restricted in the manner described above. As shown in FIG. 8, a pear-shaped rear cover plate 460 may preferably be connected to the proximal end 12b of the proximal housing 12. A first shaft hole 462 having a cross-sectional size substantially corresponding to the cross-sectional size of the drive shaft 105 is provided in a lower portion of the rear cover plate 460 for receiving the drive shaft 105 therethrough. Thus, the yoke 103 is restricted to only longitudinal movement in this arrangement because, the distal side of the yoke 103 is coupled to the mounting shafts 20a, 20b which are disposed in the mounting holes 26a, 26b, and the proximal side of the yoke 103 is coupled to the drive shaft 105 which is disposed in the first shaft hole 462.

Figure 9A:
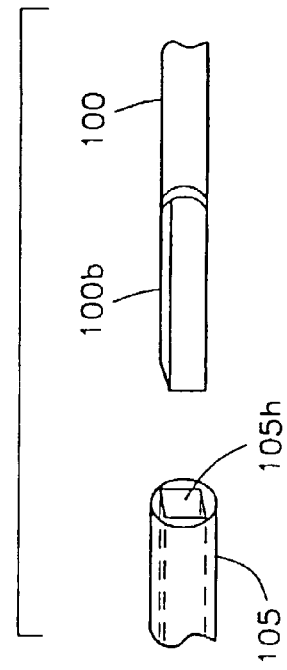
FIG. 9a shows a mechanism for restricting motion of a drive shaft of the device of FIG. 1.

As shown in FIG. 9a, the movement of the drive shaft 105 may be restricted to only rotation movement about its axis by two washer-type devices 470 fixedly attached to the drive shaft 105 on either side of the rear cover plate 460. A similar result may be achieved by providing the drive shaft 105 with a larger cross-sectional size on either side of the rear cover plate 460 in relation to the portion of the drive shaft 105 within the rear cover plate 460. Alternatively, the cross-section of a bulging portion 476 of the drive shaft 105 located substantially in the center of the rear cover plate 460 may be larger than the portions of the drive shaft 105 immediately adjacent to the bulging portion 476. The first shaft hole 462 may then have a center portion 474 with a larger cross-section than the rest of the first shaft hole 462 to accommodate the bulging portion 476 of the drive shaft 105.

Figure 9C:
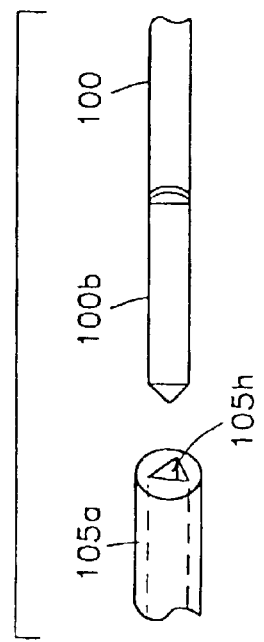
FIG. 9c shows a second coupling arrangement for the drive cable and the drive shaft in the device of FIG. 1.
Figure 9B:
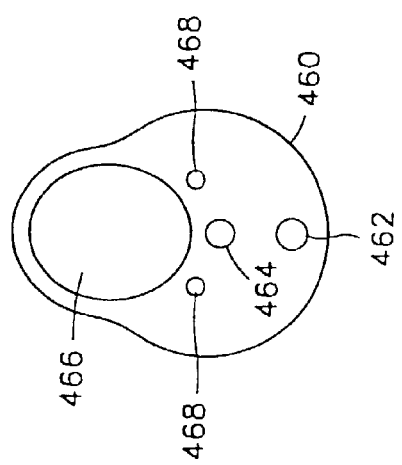
FIG. 9b shows a first coupling arrangement for a drive cable and a drive shaft in the device of FIG. 1.

FIG. 9b shows a coupling arrangement between the drive cable 100 and the drive shaft 105 in which a proximal end 105a of the shaft may have a D-shaped hole 105h extending therethrough. A distal end 102b of the drive cable 100 has a D-shape corresponding to the shape of the hole 105h so that the distal end 102b of the drive cable may be received within the hole 105h in the drive shaft 105. FIG. 9c shows an alternative coupling arrangement for coupling the drive cable 100 to the drive shaft 105 in which the hole 105h in the proximal end 105a of the drive shaft 105a and the distal end 102b of the drive cable 100 have corresponding squarish shapes. The single edge provided by the D-shapes in FIG. 9b and the four edges provided by the squarish shapes in FIG. 9c allow the drive cable 100 to transfer a rotational force to the drive shaft 105 with minimal slippage.

In operation, the user advances the endoscope 8, with the working head assembly 2 received therearound, to a portion of tissue to be resectioned until the working head assembly 2 is in a desired position adjacent to the tissue to be resectioned. The user may then apply a force to the control handle 6 to rotate the drive cable 100 which in turn rotates the drive shaft 105 to advance the yoke 103 and the anvil member 10 distally away from the distal end 12a of the proximal housing 12. As shown in FIG. 3 when the anvil member 10 has reached the distal most position, a known grasping device 108 is advanced through the sheath 4 and through the working head assembly 2 to enter the gap between the anvil member 10 and the distal end 12a via one of the grasper holes 32 and 33. Although the device in FIG. 3 is shown using a duodenoscope as the endoscope 8, those skilled in the art will understand that other types of endoscopes may also be used, such as, for example, gastroscope, colonoscope, etc.

As shown in FIG. 1, at least the distal end 12a of the proximal housing 12 preferably has a cross-section corresponding in size and shape to the proximal face 14 of the anvil member 10, including a cut-out 29 substantially corresponding in size and shape to the cut-out 13 of anvil member 10. The cut-out 29 is provided to receive the endoscope 8 therein and allow the proximal housing 12 to be slidably advanced along the endoscope 8. 20. Of course, those skilled in the art will understand that the shape of the outer surface of the working head assembly 2 may be selected in order to accommodate various desired resectioning shapes, and the shape of the anvil member 10 may preferably be selected to form a continuous surface when positioned adjacent to the proximal housing 12 to facilitate advancing the working head assembly to into and removing it from, body passages. It is preferable that the working head assembly have a maximum diameter at any point between 15 mm and 40 mm.

A tissue receiving cavity 30 is formed substantially centrally in the distal end 12a of the proximal housing 12 to facilitate the drawing of sections of tubular organs into the gap between the anvil member 10 and the distal end 12a. Those skilled in the art will understand that the depth of the cavity 30 may vary depending on the amount of tissue to be pulled into the cavity 30 and the size of the proximal housing 12. Two grasper holes 32 and 33 extend axially, preferably slightly off-center from the longitudinal axis of the proximal housing 12. In a preferred embodiment, the grasper holes 32 and 33 may each preferably receive a grasping device 108 advanced from the control handle 6, through the sheath 4, and through a respective one of the grasper holes 32 and 33.

In operation, either one or two grasping devices 108 may then be used to pull a section of the tubular organ between the anvil member 10 and the distal end 12a of the proximal housing 12 and into the cavity 30. A third grasping device 108 may also be inserted through the working channel of the endoscope 8 to provide another means of positioning the organ section between the anvil member 10 and the proximal housing 12. Of course, those skilled in the art will understand that any desired instrument may be advanced to the gap between the anvil member 10 and the distal end 12a through any of the grasper holes 32, 33 and the working channel of the endoscope 8.

A plurality of staple slits 34 are preferably disposed in two offset substantially circular rows extending along the periphery of the distal end 12a of the proximal housing 12. The staple slits 34 extend from an area adjacent to the mounting shaft 26a to an area adjacent to the other mounting shaft 26b. The plurality of staple slits 34 may preferably be arranged so that when the anvil member 10 is in the proximal most position, each of the staple slits 34 is aligned with a corresponding one of the staple-forming grooves 19.

When the device is configured for operation, a plurality of staples is received within the working head assembly 2 with each of the staples being aligned with a respective one of the staple slits 34. The staples are then sequentially fired from the respective staple slits 34 by an actuating mechanism 104 (shown in FIG. 5) disposed in the proximal housing 12.

A substantially circular blade slit 36 extends substantially radially within the staple slits 34 so that, when the anvil is in the proximal most position, the blade slit 36 is aligned with the guiding slit 21 on the anvil member. As shown more clearly in FIG. 12, extensions 84a and 84b of the blade slit 36 extend into blade housings 74a and 74b, respectively, which project distally from the distal end 12a of proximal housing 12. The blade housings 74a and 74b are preferably situated so that when the anvil member 10 is in its proximal most position, the blade housings 74a and 74b contact portions 43a and 43b of the rim 41 of the anvil member 10. The extension of the blade housings 74a and 74b from the proximal housing 12 is preferably selected so that when the blade housing devices 74a and 74b engage the remainder portions 43a and 43b of the rim 41 (thereby stopping a proximal movement of the anvil member 10 and defining the proximal most position thereof), a gap is formed between the anvil member 10 and the distal end 12a of a length sufficient to allow the anvil member 10 to securely hold a portion of the organ against the proximal housing 12 without crushing and damaging the portion of the organ.

When positioned at one end of the blade slit 36 (i.e., in one of the extensions 84a and 84b), a cutting blade 202 is preferably completely enclosed within the respective one of the blade housing devices 74a and 74b and the guiding slit 21, so that the cutting blade 202 does not cut any tissue until the physician intentionally operates the blade 202. When the physician operates the blade 202, the blade 202 is driven from its initial position received within one of the extensions 84a and 84b around the blade slit 36 with its cutting edge facing a direction of movement, until the blade 202 is received into the other one of the extensions 84a and 84b. Thus, after a cutting operation has been performed, the blade 202 is once again prevented from inadvertently injuring the patient.

Figure 6:
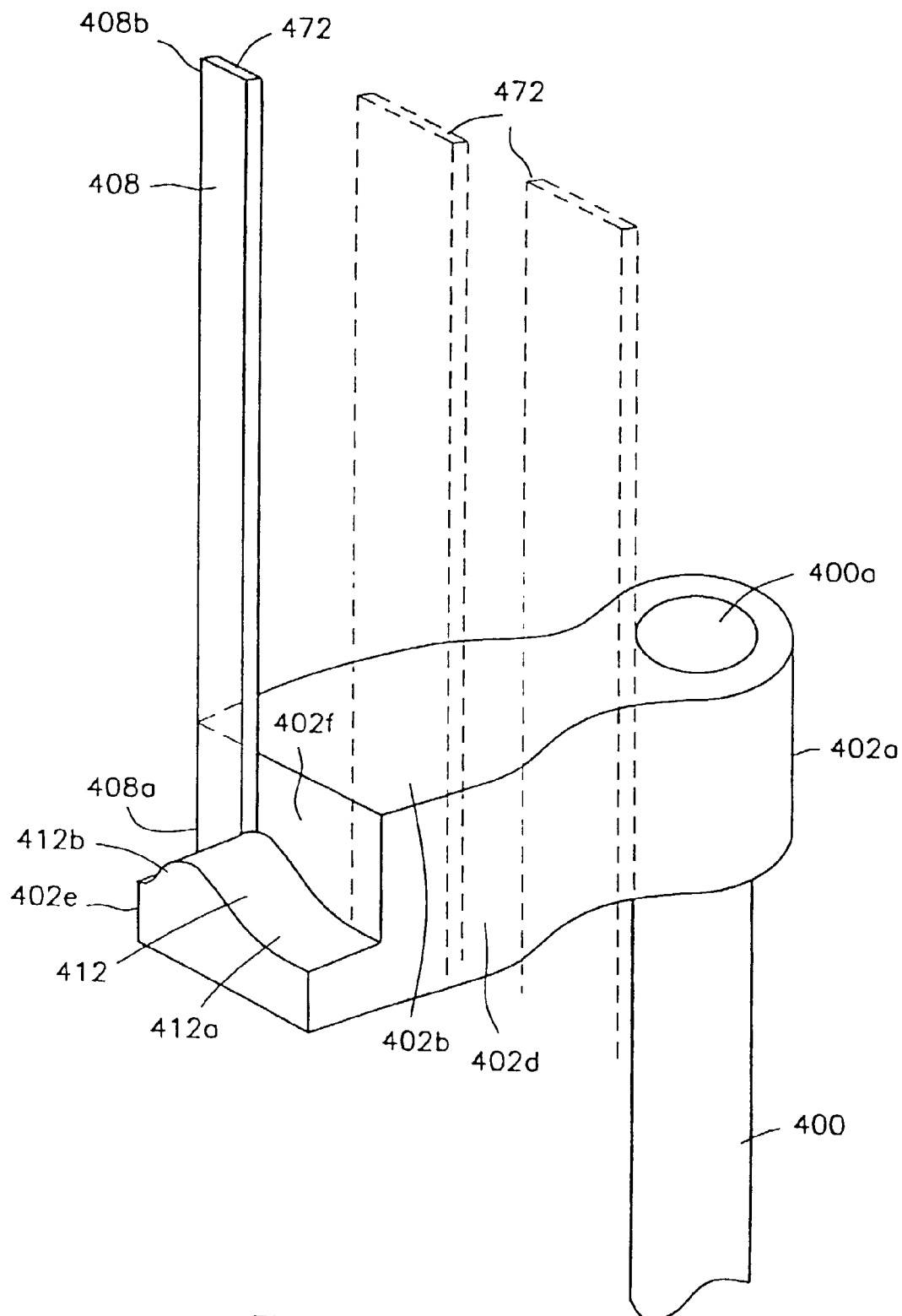
FIG. 6 shows a detailed view of the wedge used in the actuating mechanism of FIG.
Figure 7:
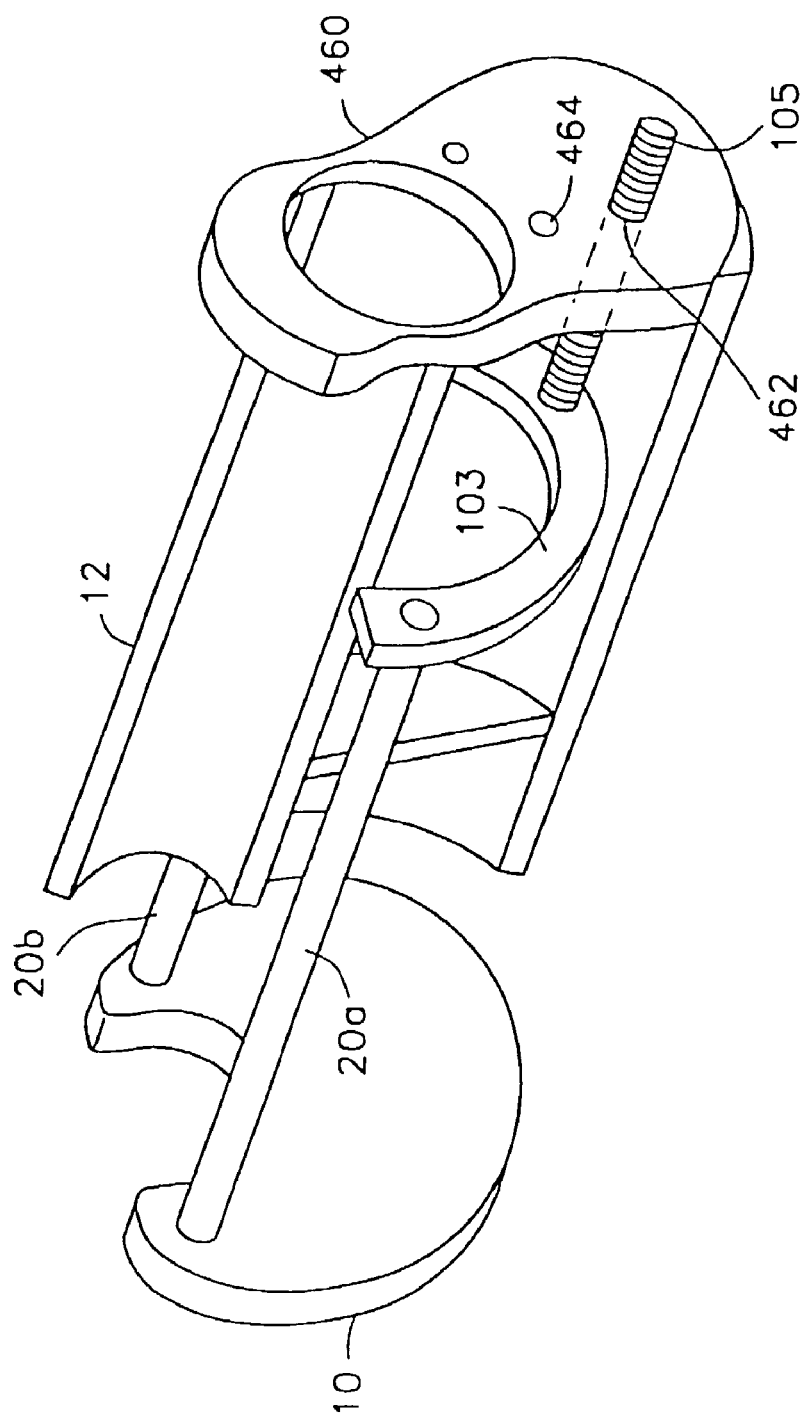
FIG. 7 shows a cut-away view of a working head assembly of the device of FIG. 1.

FIG. 6 shows a wedge 402, a first portion 402a of which is non-rotatably coupled to an actuating shaft 400 so that rotation of the shaft 400 the wedge 402 rotates, preferably about the longitudinal axis of the working head assembly 2. The wedge 402 includes a blade handle 408 which extends from a first portion 408a coupled to the wedge 402 to a second portion 408b which is coupled to the blade 202 so that, when the wedge 402 is rotated, the blade 202 is rotated through the blade slit 36. The wedge 402 has a substantially bell-like cross-section when viewed axially, with a second portion 402b extending radially outward from the first portion 402a and, consequently, from the longitudinal axis of the shaft 400 which preferably coincides with the longitudinal axis of the working head assembly 2. A notch of varying depth is cut out of a radially outer portion of the second portion 402b to form a cam surface 412 thereon. A first ramp section 412a ramps up from a leading face 402d of the wedge 402 to adjoin a second ramp section 412b that ramps down to adjoin a rear face 402e of the wedge 402. The wedge 402 is preferably arranged in the proximal housing 12 so that the cam surface 412 is substantially aligned with the staple slits 34.

A staple driver 472 extends substantially longitudinally, proximally from each of the staple slits 34 having toward the plane in which the wedge 402 rotates and each staple driver 472 is slidably received within the working head assembly 2 for motion between a distal most, staple driving position and a proximal most inoperative position. In the inoperative position, an upper end of each of the staple drivers 472 is completely received within the proximal housing 12, just proximal of a respective staple. The staple drivers 472 are preferably substantially rectangular in shape, although bottom edges 472a thereof may more preferably be rounded. The length of the staple drivers 472 is preferably selected so that, in the inoperative position, the bottom surfaces 472a extend into the plane of rotation of the wedge between the proximal and distal most extents of the first ramp portion 412a. The bottom surfaces 472a are, in the inoperative position, more preferably substantially aligned with the distal most projection of the of the cam surface 412 at the leading face 402d. Thus in operation, the wedge 402 is rotated by the actuating shaft 400 so that the first ramp section 412a of the cam surface 412 successively drives each of the staple drivers 472 into contact with a corresponding staple so that each staple driver 472 and its staple are driven distally through a respective one of the staple slits 34. This drives the staples across the gap from the distal end 12a into the anvil member 10, through any tissue held between the anvil member 10 and the proximal housing 12, and into the corresponding staple forming grooves 19. Thus the section of the tissue gripped between the anvil member 10 and the proximal housing 12 is stapled in a pattern substantially the same as that formed by the staple slits 34 (i.e., substantially circular). At the same time, the blade 202 is rotated through the blade slit 36 to cut the tissue which has just been stapled through the rotation of the wedge 402.

After each of the plurality of staples has been fired, the wedge 402 may be driven in a reverse direction 20. to reload a new plurality of staples. The wedge 402 may rotate in a direction opposite the staple firing direction without getting caught on any of the staple drivers 472 because the staple drivers are pushed out of the way by the second ramp section 412b of the cam surface 412.

In operation, the user applies a force to the control handle 6 to rotate an actuating cable 450 about its longitudinal axis. This rotational force is transferred to the actuating shaft 400, which then rotates the wedge 402 around the longitudinal axis of the actuating cable 450. The first ramp section 412a of the cam surface 412 of the wedge 402 then individually drives the staple drivers 472 distally as described above to staple the tissue received between the anvil member 10 and the proximal housing 12 with the cutting blade 202 lagging behind the firing of the stapling since the blade handle 408 is coupled to the rear face 402e of the wedge.

Figure 10A:
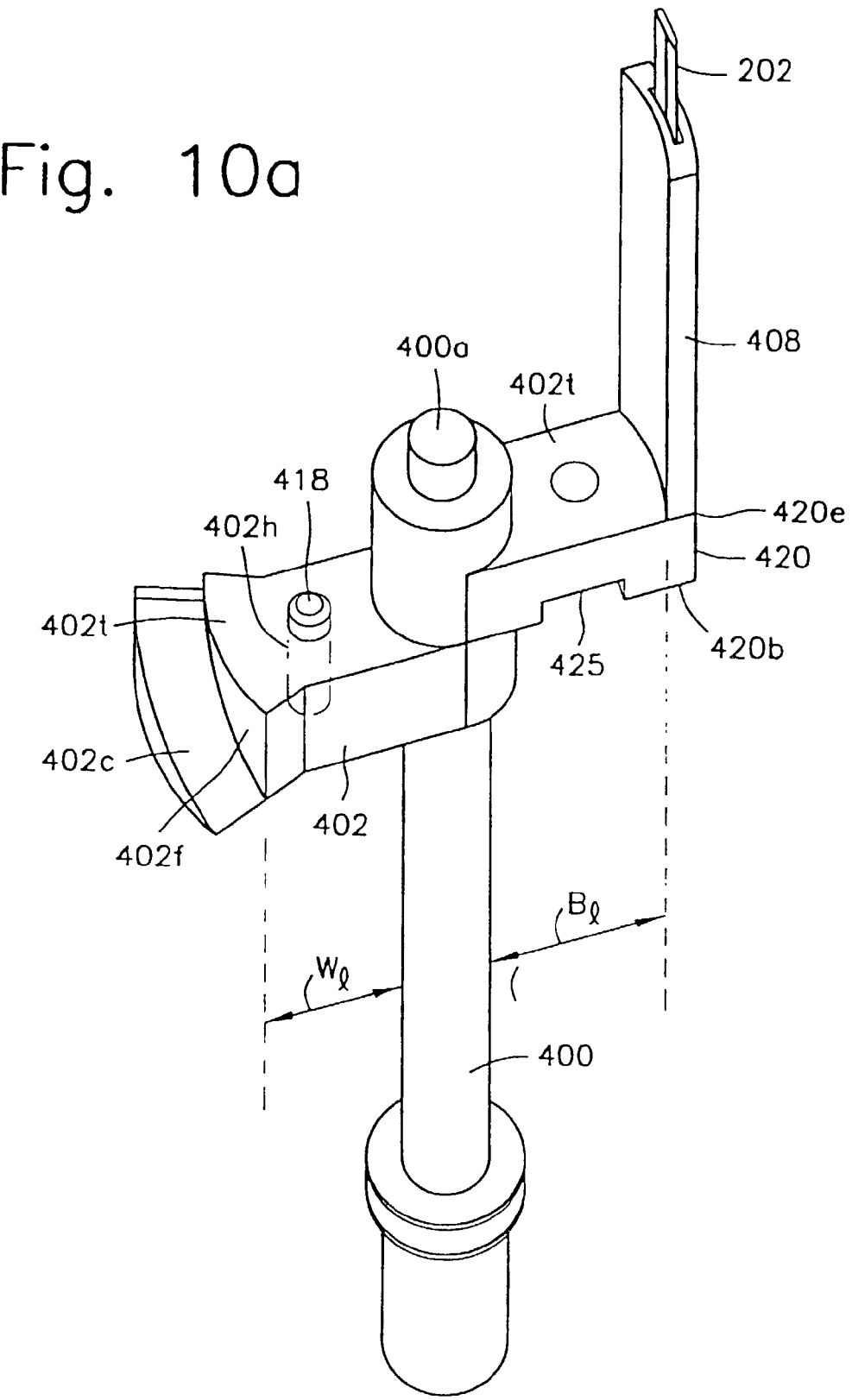
FIG. 10a shows a perspective view of an alternative construction of the wedge of FIG. 6.

FIG. 10a shows an alternative configuration of the wedge 402 of FIG. 6 including a separate blade portion 420. The blade portion 420 is preferably rotatably coupled to the distal end 400a of the actuating shaft 400 so that a rotation of the actuating shaft 400 about its longitudinal axis does not cause a corresponding rotation of the blade portion 420. As in FIG. 6, the wedge 202 of this apparatus is non-rotatably coupled to the distal end 400a of the shaft 400.

The blade handle 408 of this apparatus, which is coupled to a peripheral edge 420e of the blade portion 420, extends to the cutting portion of the blade 202. As described above, the cutting portion of the blade 202 extends past the distal end 12a except when the blade 202 is received within one of the extensions 84a and 84b.

Figure 10B:
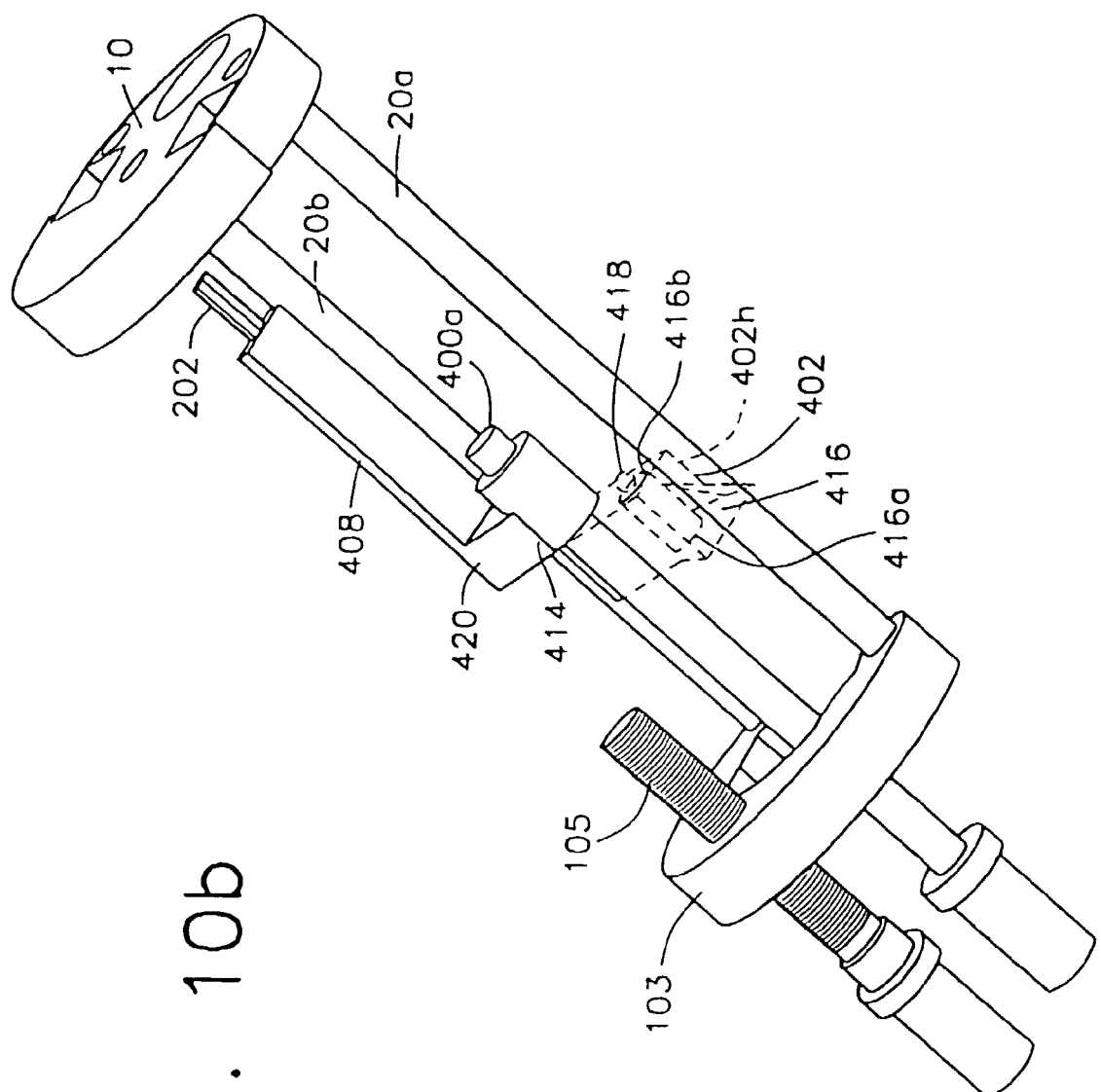
Figure 10C:
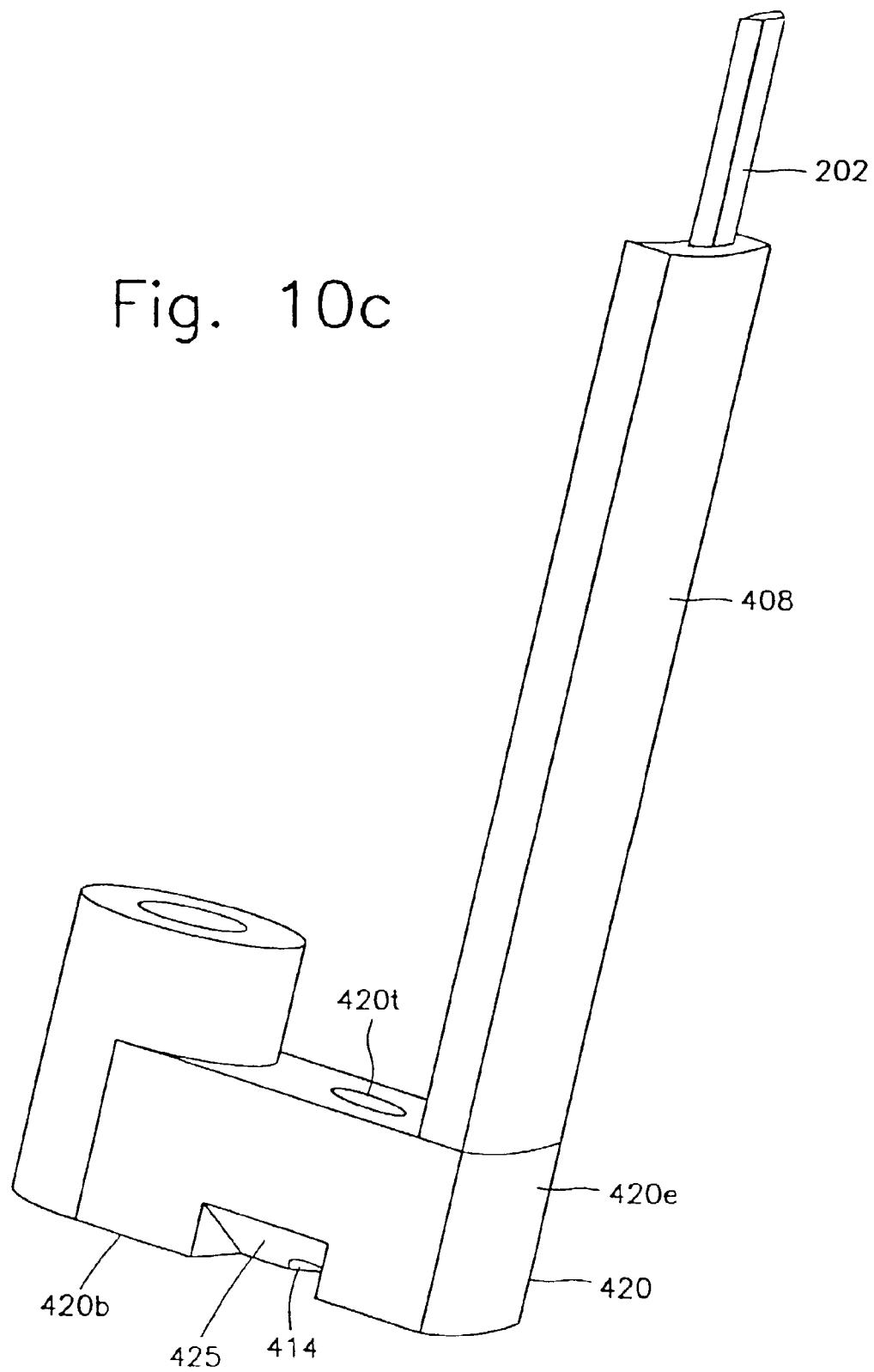

The wedge 402 substantially corresponds in shape and size to the wedge 402 of FIG. 6, except that the blade handle 408 is not coupled thereto. In addition, a locking shaft 402h extends into a distal surface 402t located as shown in FIG. 10a so that when the blade portion 420 and the wedge portion 410 are aligned, the locking shaft 402h and a locking dimple 414 (shown in FIG. 10c) on the bottom face 420b of the blade portion 420 are substantially aligned. As shown in FIG. 10b, a spring 416 is received within the locking shaft 402h with a proximal end of the spring coupled to the proximal end of the locking shaft 402h. A locking ball 418 coupled to the distal end 416b of the spring 416 is sized so that when a proximally directed force is applied to the locking ball 418, the locking ball 418 may be slidably received within the locking shaft 402h. In addition, when no distally directed force is applied to the locking ball 418, the spring 416 preferably extends so that approximately one half (or more) of the locking ball 418 extends distally out of the locking shaft 402h. Thus, when the wedge 402 is rotated toward the blade portion 420, the locking ball 418 is received in a cut-out 425 formed on the proximal surface 420b of the blade portion 420. As shown in FIG. 10c, the cut-out 425 slopes downward to adjoin the locking dimple 424 so that when the locking ball 418 is received, the slope of the cut-out 425 gradually pushes the locking ball 418 into the locking shaft 420h. Then, when the wedge 402 moves into alignment with the blade portion 420, the locking ball 418 extends out of the locking shaft 402h and enters the locking dimple 414 to couple the wedge 402 to the blade portion 420 so that a rotation of the wedge 402 causes a corresponding rotation of the blade portion 420.

A radial length $B_1$ between the peripheral edge 420e of the blade portion 420 and the actuating shaft 400 may substantially correspond to a radial length $W_1$ between the wall 402f of the wedge portion 410 and the actuating shaft. This places the blade handle 408 in substantially the same position, relative to the cam surface 402c of the wedge portion 410, as in the previous embodiments. Of course, those skilled in the art will understand that it is important that the blade 408 should extend substantially distally to the blade slit 36 so that rotation of the blade portion 420 will cause a corresponding rotation of the blade 202 through the blade slit 36.

In operation, the wedge 402 is initially situated distally of one of the blade housings, e.g., 74a while the blade portion 420 is situated dally of the blade housing 74b with the blade 202 received in the blade housing 74b. When the lesion tissue has been drawn into position between the distal end 12a and the anvil member 10, the physician actuates the shaft 400 by applying a force at the control handle 6. This causes the wedge portion 410 to rotate distally of the staple slits 34, to sequentially drive each of the staple drivers 472 distally through the corresponding staple slit 34. When the wedge 402 has rotated fully into alignment with the blade portion 420 and the locking ball 418 is received into the locking dimple 414, the operator then operates the control handle 6 in the opposite direction to draw the blade 202 out of the blade housing 74b to cut all of the tissue extending radially inward of the rows of staples. When the blade 202 is received in the other blade housing 74a, the wall of the body passage is released and the lesion tissue remains within the gap between the distal end 12a and the anvil member 10 held by the grasping devices 108. The lesion tissue may then be withdrawn from the body for analysis. This embodiment of the wedge 402 provides a safeguard in case the stapling process must be prematurely aborted due to, for example, a jam in one of the staple slits 34. Using this embodiment, the cutting process is not begun until all of the staples have been fired. Thus, it is possible to reduce the risk of cutting an opening in an organ which is not completely closed by the staples.

Figure 5:
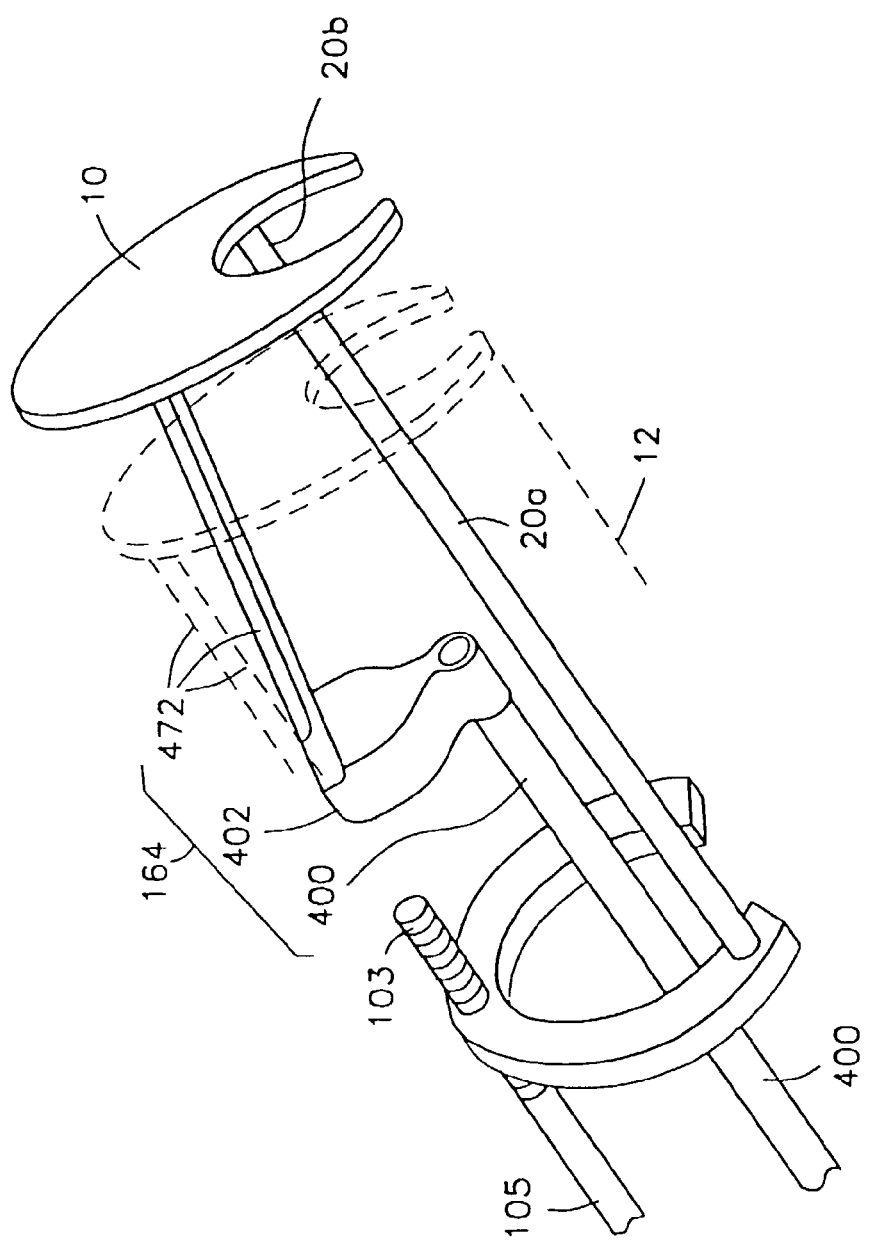
FIG. 5 shows a cutaway of the device of FIG. 1 showing an actuating mechanism.

As shown in FIG. 5, the actuating mechanism 104 includes the actuating cable 450 which extends from a proximal end 450a coupled to the control handle 6 to a distal end 450b coupled to the proximal end 400a of the actuating shaft 400. Those skilled in the art will understand that the wedge 402 should preferably be situated towards the distal end 12a of the proximal housing 12 so that the yoke 103 does not interfere with 20. rotation of the wedge 402 around the longitudinal axis of the actuating shaft 400 (discussed below) even when the yoke 103 is in its distal most position.

As shown in FIGS. 7–9a, the rear cover plate 460 may preferably be coupled to the proximal end 12b of the proximal housing 12. The proximal end 12b of the proximal housing 12 is then connected to the sheath 4. The actuating shaft 400 may preferably extend through a second shaft hole 464 formed in the rear cover plate 460 of the proximal housing 12 and preferably abuts an interior portion of the cavity 30 provided on the proximal housing 12. An endoscope hole 466 may preferably be provided on a portion of the rear cover plate 460 radially separated from the longitudinal axis of the working head assembly 2 to guide the endoscope 8 into the cut-out 29 of the proximal housing 12. The endoscope 8 may preferably be received into the endoscope hole 466 from an endoscope lumen 40 provided within the sheath 4 which is preferably disposed along a periphery of the sheath.

Figure 9D:
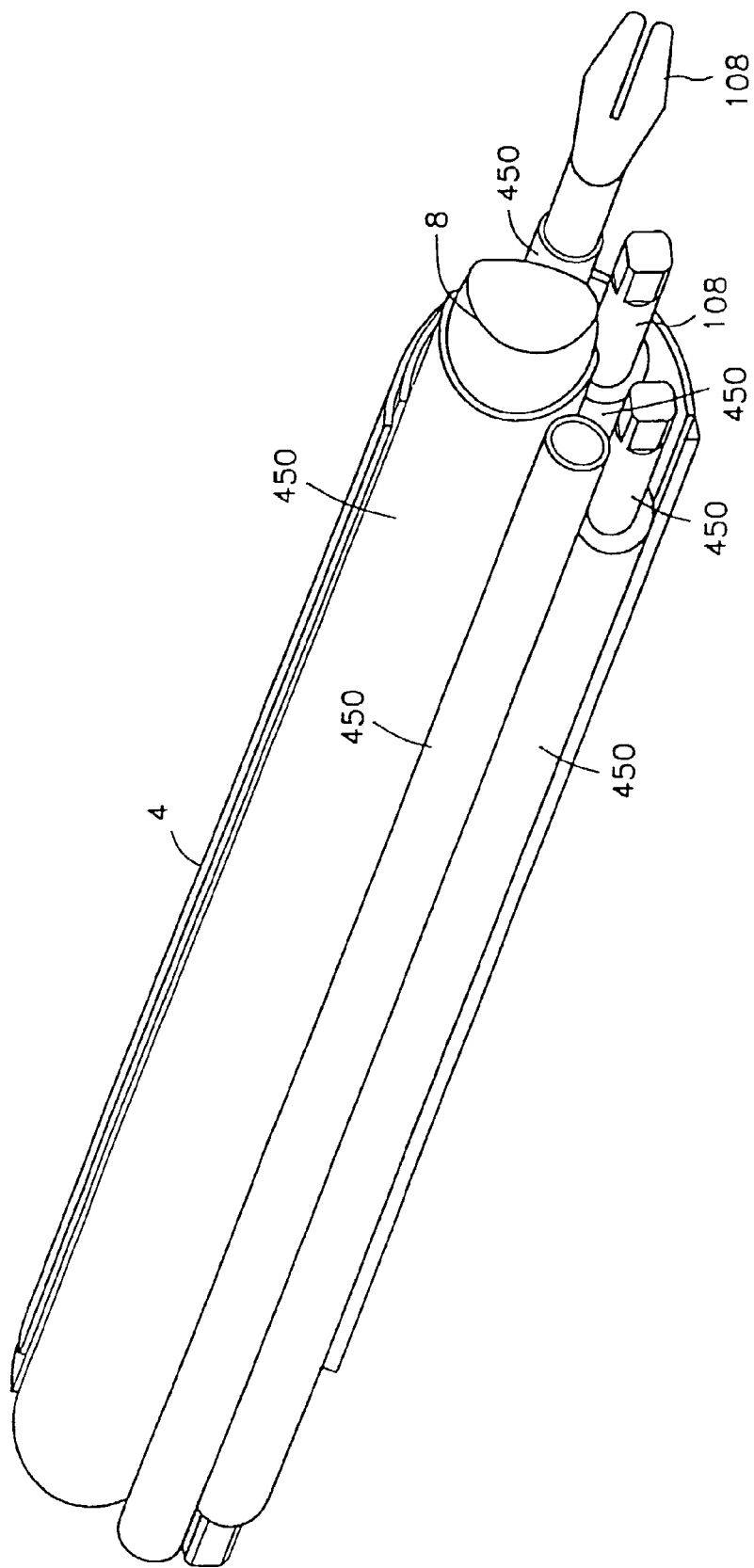
FIG. 9d shows a perspective cut-away view of a sheath of the device of FIG. 1.

FIG. 9*d* shows a perspective cut-away view of the sheath 4 with the various devices (i.e., the two grasping devices 108, the drive cable 100, the actuating cable 450, and the endoscope 8) extending therethrough. Each of the various devices are further enclosed by one of a plurality of tubes 510 which allow either a rotational movement (for the cables 100, 450) or a longitudinal (for the two grasping devices 108 and the endoscope 8) movement therein. Similar to the sheath 4, the plurality of tubes extend from a proximal end coupled to the control handle 6, to a distal end coupled to the working head assembly 2. The plurality of tubes 510 provide protection against damage due to, for example, abrasion, and provide an isolated path through the sheath 4 which prevents tangling between the various devices.

Figure 18:
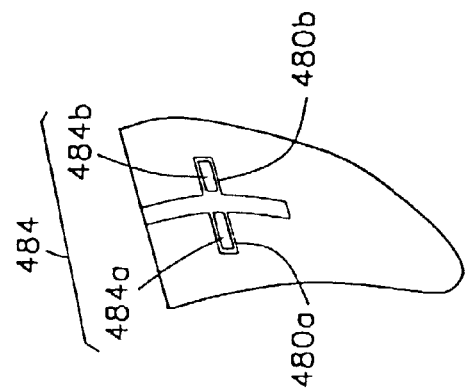
FIG. 18 shows a second arrangement of the blade shield for use with a device according to the present invention.

FIG. 18 shows a cross-section of the control handle 6 which may be used in conjunction with a resectioning device of the invention. The control handle 6 may preferably be substantially "Y" shaped, with a first branch 500 for operating the actuating mechanism 104 and a second branch 502 for operating the drive mechanism 102 and a body 520. A receiving hole 512 runs longitudinally through the center of the body 520 for receiving the endoscope 8 therethrough. A first force transferring mechanism 504 is coupled to an actuating control knob 508, and extends axially through the first branch 500, through the body 520, where it is coupled to the actuating cable 450 which extends through the sheath 4 to connect to the actuating mechanism 104. A second force transferring mechanism 506 is coupled to a drive control knob 510, and extends axially through the second branch 502, through the body 520, where it is coupled to the drive cable 100 which extends through the sheath 4 to the drive mechanism 102. Those skilled in the art will understand that the control handle may be designed in any variety of shapes to accommodate, for example, different hand sizes, comfort, etc. In addition, different force transferring methods may also be used instead of a knob such as, for example, actuating levers, etc.

In operation, the user applies a rotational force to one of the control knobs 508 and 510, the rotational force is transferred through a respective one of the force transferring mechanisms 504 and 506 which then transfers rotational force to a respective one of the drive cable 100 and actuating cable 450, thereby operating the actuating mechanism 104 or the drive mechanism 102 as described above.

Figure 11:
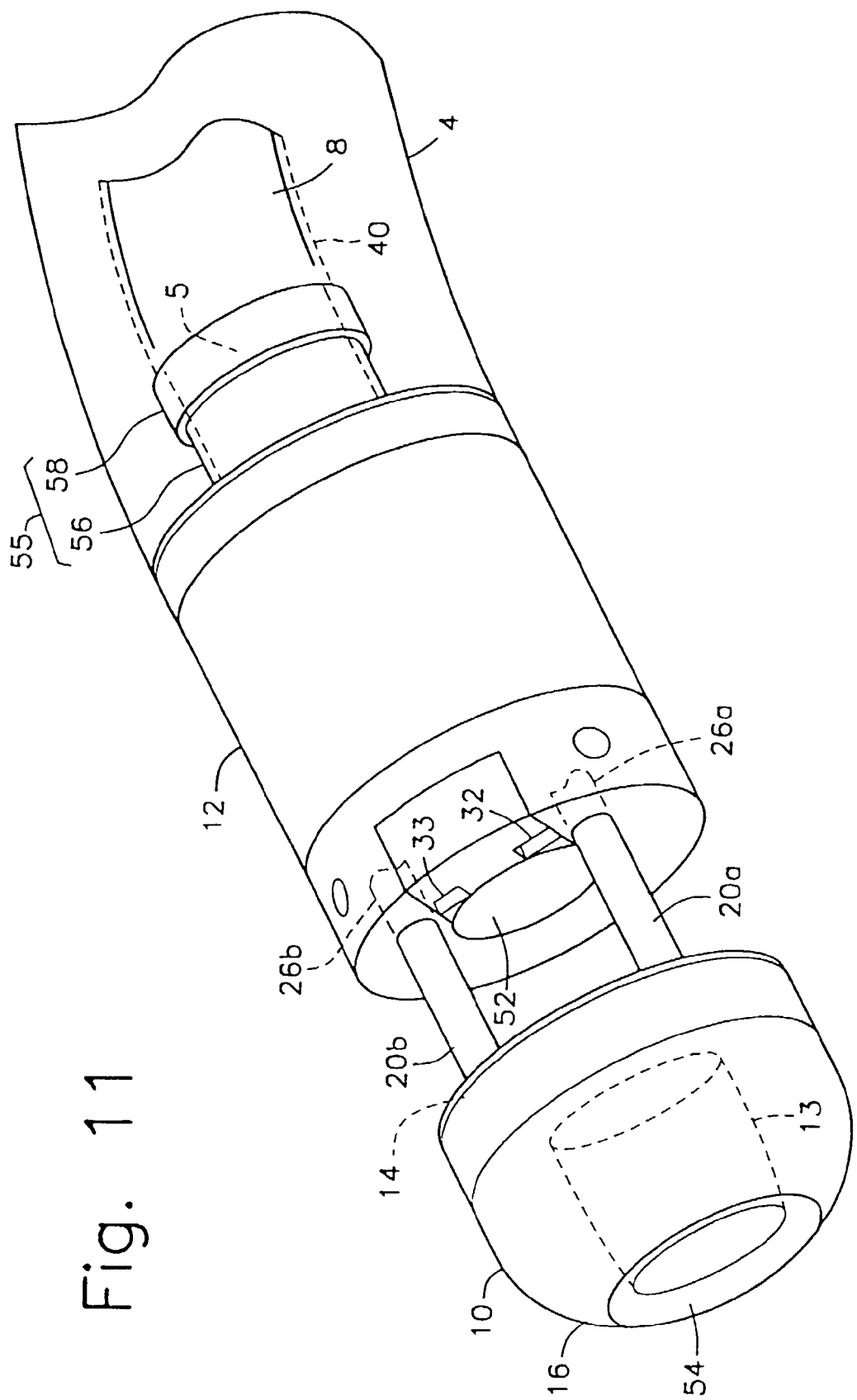
FIG. 11 shows a device according to a second embodiment of the present invention.

FIG. 11 shows a device according to a second embodiment of the present invention in which like reference numerals identify the same elements.

The anvil member 10 of this embodiment preferably has a substantially circular or elliptical cross-section and is gradually tapered from the proximal face 14 to its distal end 16, forming a bullet-like structure. This tapered shape allows the device to be more easily inserted into the patient's body as the distal end 16 has a smaller cross-sectional size than in the first embodiment. Those skilled in the art will understand that the anvil member 10 may have other tapered shapes besides a bullet-like structure without departing from the scope of the present invention.

Instead of providing the cut-out 13 shown in the first embodiment to receive the endoscope 8 therein, a substantially cylindrical first endoscope lumen 13 extends axially through the center of the anvil member 10. The distal end 16 of the anvil member 10 may preferably have a beveled edge 54 adjoining the first endoscope lumen 13 to allow for an expanded field of forward vision via the endoscope 8.

The proximal housing 12 may preferably have a cross-section corresponding in size and shape to the cross-section of the proximal face 14 of the anvil member 10 (i.e., substantially circular or elliptical). In this embodiment, the cavity 30 in the first embodiment has been omitted and a substantially cylindrical second endoscope lumen 52 extends axially through the center of the proximal housing 12.

However, as in the previous embodiment, two grasper holes 32, 33 extend axially through the proximal housing. The two grasper holes 32 and 33 may preferably be disposed between the mounting holes 26*a* and 26*b* since the first endoscope lumen 13 now extends through the axial center of the proximal housing 12. In addition, the grasper holes 32, 33 in this embodiment may preferably have a substantially circular cross-section. However, those skilled in the art will understand that the cross-sectional shape of the grasper holes 32 and 33 may be selected to, for example, accommodate another type of device.

A receiving sleeve 55 is provided on the proximal end 12*b* of the proximal housing 12 for receiving the endoscope 8 and for guiding the endoscope 8 into the proximal housing 12. The receiving sleeve 55 may preferably have a first section 56 and a second section 58. The first section 56 and second section 58 may preferably both have an annular cross-section forming a continuous center hole 59 therethrough. The center hole 59 has a diameter which preferably corresponds to the diameter of the receiving hole 52 so that the endoscope 8 may be continuously received through the center hole 59 into the second endoscope lumen 52 in the proximal housing 12 The second section 58 preferably has a thicker wall than the first section 56, such that an annular ring formed by the cross-section of the second sections 58 has a larger width than an annular ring formed by the cross-section of the first section 56.

In contrast to the endoscope lumen 40 disposed along the periphery of the sheath 4 as shown in FIG. 1, the endoscope lumen 40 in this embodiment preferably runs along an axial center of the sheath 4, so that when the sheath 4 is coupled to the working head assembly 2, a substantially continuously aligned path is formed through the center hole 59, through the second endoscope lumen 52, and through the first endoscope lumen 13. The actuating shafts 400 and 105 and the drive cables 450 and 102 are then located concentric to the endoscope lumen 40 in the sheath 4.

Figure 12:
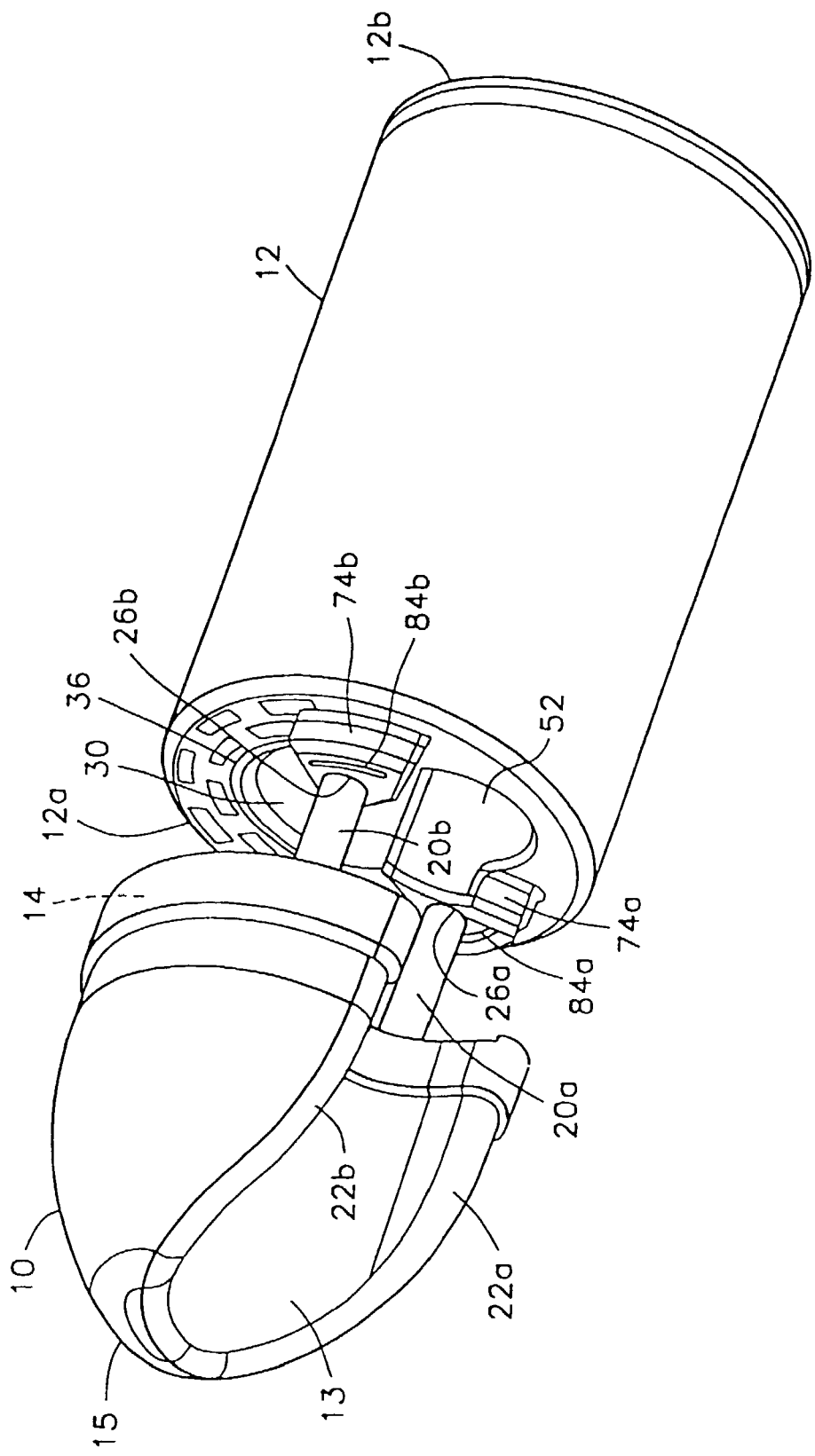
FIG. 12 shows a device according to a third embodiment of the present invention.

FIG. 12 shows a device according to a third embodiment of the present invention. The proximal face 14 of the anvil member 10 of this embodiment has a cross-section similar to the crescent-shaped cross-section of the anvil member 10 of the device of FIG. 1. Thus, the anvil member 10 has two horns 22*a* and 22*b* formed on either side of a cut-out 13 which extends axially through the anvil member 10 from the proximal face 14 to the distal end 15 to receive the endoscope 8 therein. As with the device of FIG. 11, the cross-sectional size of the anvil member 10 diminishes in overall size from a maximum at the proximal face 14 to a minimum size at the distal end 15, and the horns 22*a* and 22*b* become less pronounced from the proximal face 14 to the distal end 15. In a side view, the anvil member 10 becomes gradually tapered from the proximal end 14 to the distal end 16.

As in the device of FIG. 11, the tapered shape of the anvil member 10 of the device of FIG. 12 allows for easier insertion of the device into the patient's body. In contrast to the second embodiment, the cut-out 13 provides a larger field of vision via the endoscope 8 as the anvil member does not totally enclose the cut-out 13. And, as in the first embodiment, two substantially cylindrical mounting shafts 20a and 20b are coupled to the proximal face 14 of the anvil member 10 on horns 22a and 22b and are received within the mounting holes 26a and 26b, respectively.

In contrast to the previous embodiments, the proximal housing 12 in this embodiment may preferably have a substantially oval cross-sectional shape. This shape of the proximal housing 12 is formed by extending the proximal housing 12 shown in FIG. 1 around the cut-out 29 to create the substantially cylindrical second endoscope lumen 52. The oval shape allows the second endoscope lumen 52 to be offset from the axial center of the proximal housing 12 and aligned with the first endoscope lumen 13. This offset of the second lumen 52 allows the cavity 30 to be provided adjoining the blade slit 36. In all other material respects, the proximal housing 12 in this embodiment is substantially identical to the proximal housing 12 illustrated in FIG. 1.

Figure 13:
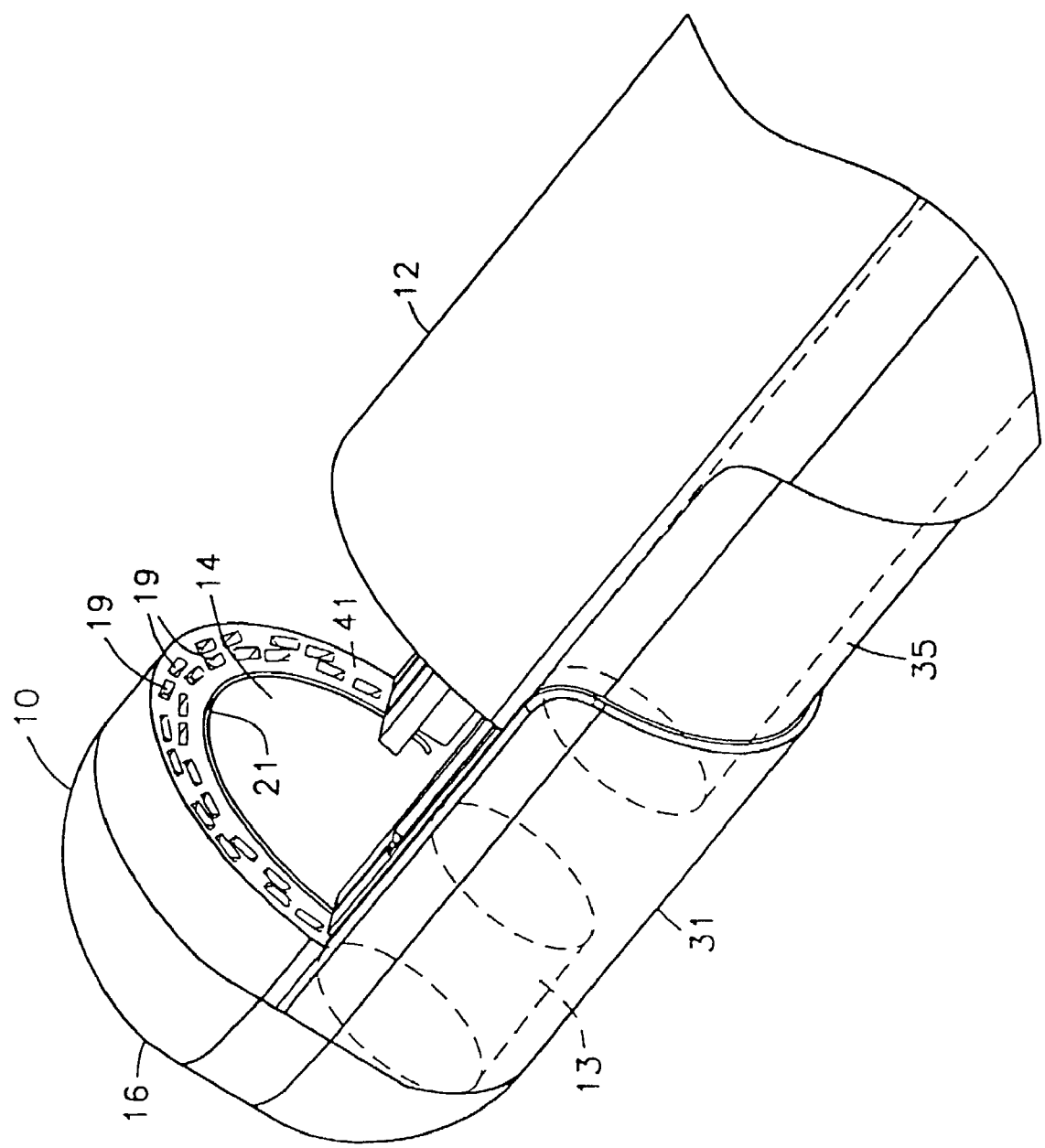
FIG. 13 shows a device according to a fourth embodiment of the present invention.

FIG. 13 shows a device according to a fourth embodiment of the present invention. This embodiment is substantially similar to the embodiment shown in FIG. 12. However, the proximal face 14 of the anvil member 10 in this embodiment has a substantially oval-shaped cross-section corresponding to the proximal housing 12. The anvil member 10 is tapered towards the distal end 16 to form a substantially bullet-like structure having an oval-shaped cross-section. The cut-out 13 shown in FIG. 12 may preferably be enclosed within the anvil member 10 and thereby forms an extension of the first endoscope lumen 13.

A substantially semicircular shield 31 extends from the proximal face 14 of the anvil member 10 and shields a hemispherical portion of the gap formed between the anvil member 10 and the proximal housing 12. The shield 31 allows a tissue section to be drawn primarily in the gap between the staple-forming grooves 19 and the staple slits 34 with minimal spill-over into the rest of the gap.

A recessed groove 35 may preferably be formed around a portion of the proximal housing 12 for slidably receiving the shield 31 therein. The recessed groove 35 may preferably have a size and shape substantially corresponding to the size and shape of the shield 31 so that when the anvil member 10 is in its proximal most position, the shield 31 is received within the recessed groove 35 to form a substantially completely continuous outer surface of the proximal housing 12.

In operation, the user may utilize suction through the endoscope 8 to draw a tissue section into the gap between the anvil member 10 and the proximal housing 12. In such a situation, the shield 31 prevents a portion of the tissue section or loose debris from being pulled into the area around the mounting shafts 20a and 20b which may otherwise interfere with the axial movement of the mounting shafts 20a, 20b. In addition, the shield 31 also serves to direct the pulling force of the suction to pull tissue primarily in the gap between the staple-forming grooves 19 and the staple slits 34.

Figure 14A:
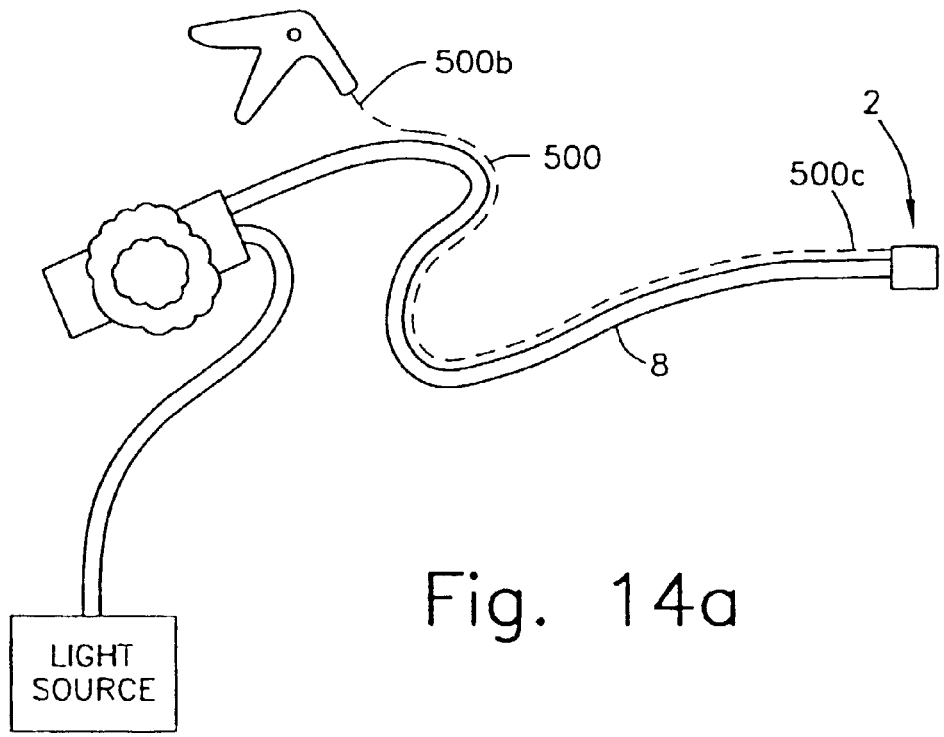
FIG. 14a shows a device according to a fifth embodiment of the present invention.
Figure 14B:
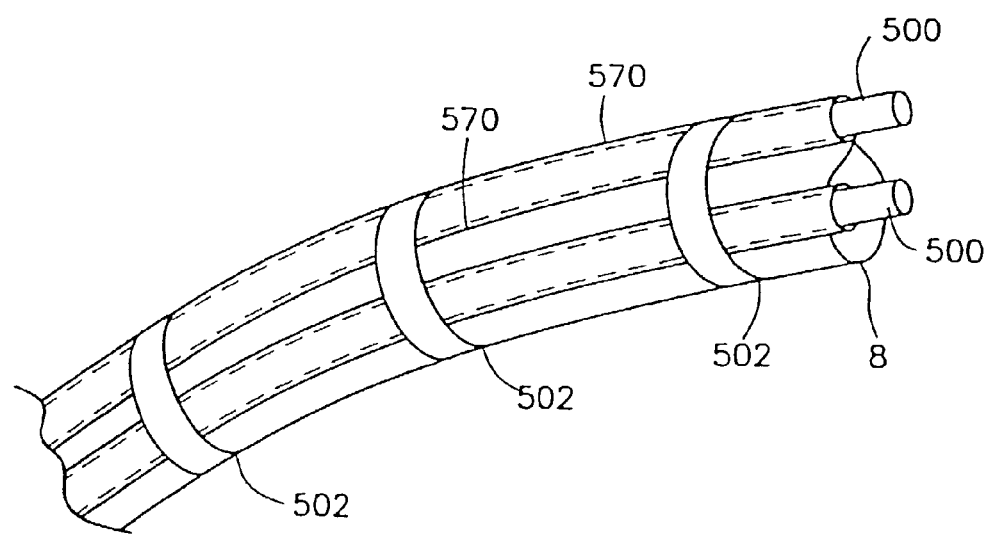
FIG. 14b shows a detailed cut-away view of the device of FIG. 14a and a conventional endoscope.

FIGS. 14a and 14b show a device according to a fifth embodiment of the present invention in which the working head assembly 2 is coupled to the endoscope 8 without the sheath 4. As described above, distal ends 500a of control cables 500 (i.e., drive cable 100 and actuating cable 450) may preferably be coupled to the working head assembly 2 while proximal ends 500b of the control cables 500 are coupled to the control handle 6 as in the previous embodiments. However, instead of using a flexible sheath 4 to receive the control cables 500 and the endoscope 8, the control cables 500 are inserted into respective tubes 510. Each of the tubes 510 should have a sufficient cross-section to allow the control cables 500 to rotate within the tubes 510. The tubes 510 are then fastened at various predetermined points along their lengths to the endoscope 8 by a plurality of fasteners 502. Those skilled in the art will understand that many different types of fasteners may be used either alone or in combination for this purpose so long as the fasteners do not impede the steering of the endoscope 8 or the rotation of the cables 500. Those skilled in the art will understand that tape (e.g., surgical, electrical, etc.), electrical cable, rubber bands, other belt-style fasteners, etc. may be used as fasteners.

Figure 17:
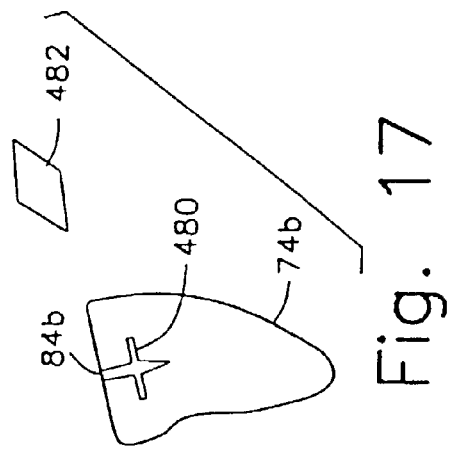
FIG. 17 shows a first arrangement of a blade shield for use with a device according to the present invention.
Figure 16:
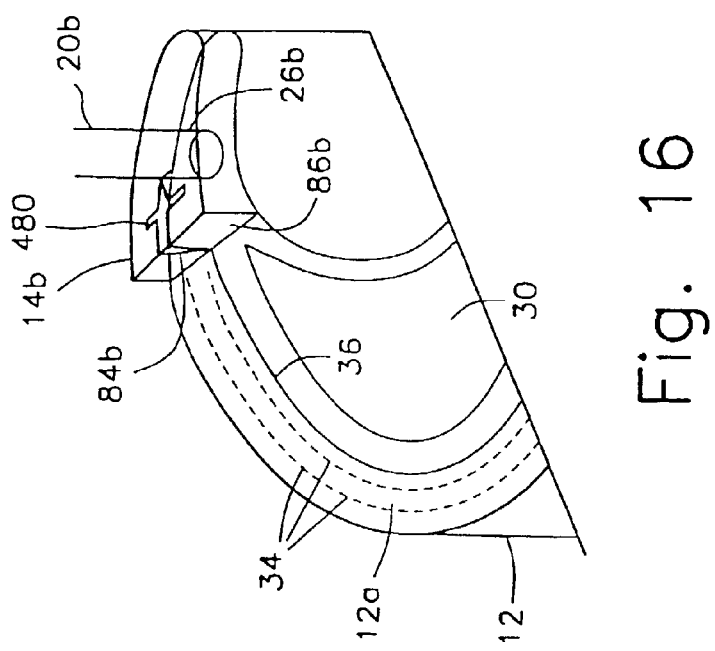
FIG. 16 shows a blade housing arrangement for use with a device according to the present invention.

FIGS. 16–18 illustrate alternative configurations of the blade housing 74b and it will be understood that similar alternative embodiments may be implemented for the blade housing 74a.

The blade slit 36 continues through the blade housing 74b into housing porion 84b which extends from a forward end at which the blade slit 36 enters the blade housing 74b to a rearward end where the blade slit 36 and the housing portion 84b terminate. A shield receiving slit 480 extends through the blade housing 74b substantially perpendicular to the housing portion 84b between the forward and rearward ends thereof.

After an organ section has been stapled between the anvil member 10 and the proximal housing 12, and the blade 202 is drawn through the stapled tissue, there may be a problem if tissue stretches along with the blade 202 into the housing portion 84b without being completely severed. Withdrawal of the resectioned tissue might then lead to tearing of the tissue which is to remain in place.

As seen in FIG. 17, a flexible breakaway shield 482 having a shape and size substantially corresponding to the shape and size of the shield receiving slit 480 is inserted into the shield receiving slit 480. After entering the housing portion 84b, the cutting blade 202 contacts the shield 482 and further progress of the blade 202 deforms the shield 482 until the shield 482 is cut in half. When the shield 482 is cut in half, each half snaps back pulling the tissue in a direction opposite the direction of travel of the blade allowing the cutting blade 202 to completely sever the tissue.

FIG. 18 shows a second alternative arrangement in which a flexible gate 484, having a first gate half 484a and a second gate half 484b, may be removably or fixedly mounted within the shield receiving slit 480. Each of the halves 484a and 484b may preferably be mounted within a respective half of the shield receiving slit 480, so that a small gap formed therebetween substantially corresponds in width to the width of the cutting blade 202. The wiping action in a direction opposed to the direction of travel of the blade 202 is substantially the same as that of the shield 482 without requiring the severing and replacement of the shield 482 after each use.

Figure 19A:
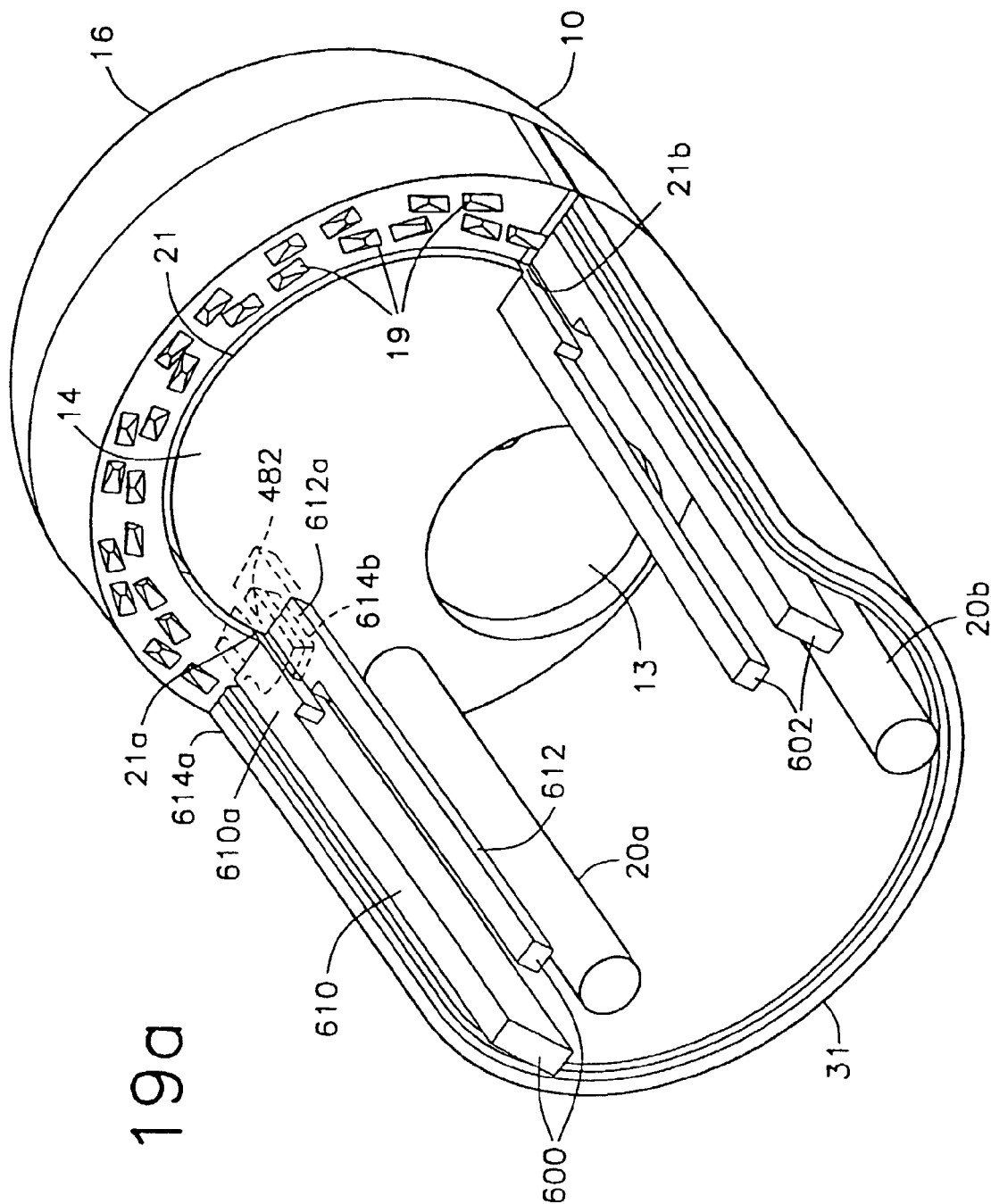
FIG. 19a shows a third arrangement of the blade shield for use with a device according to the present invention.
Figure 19B:
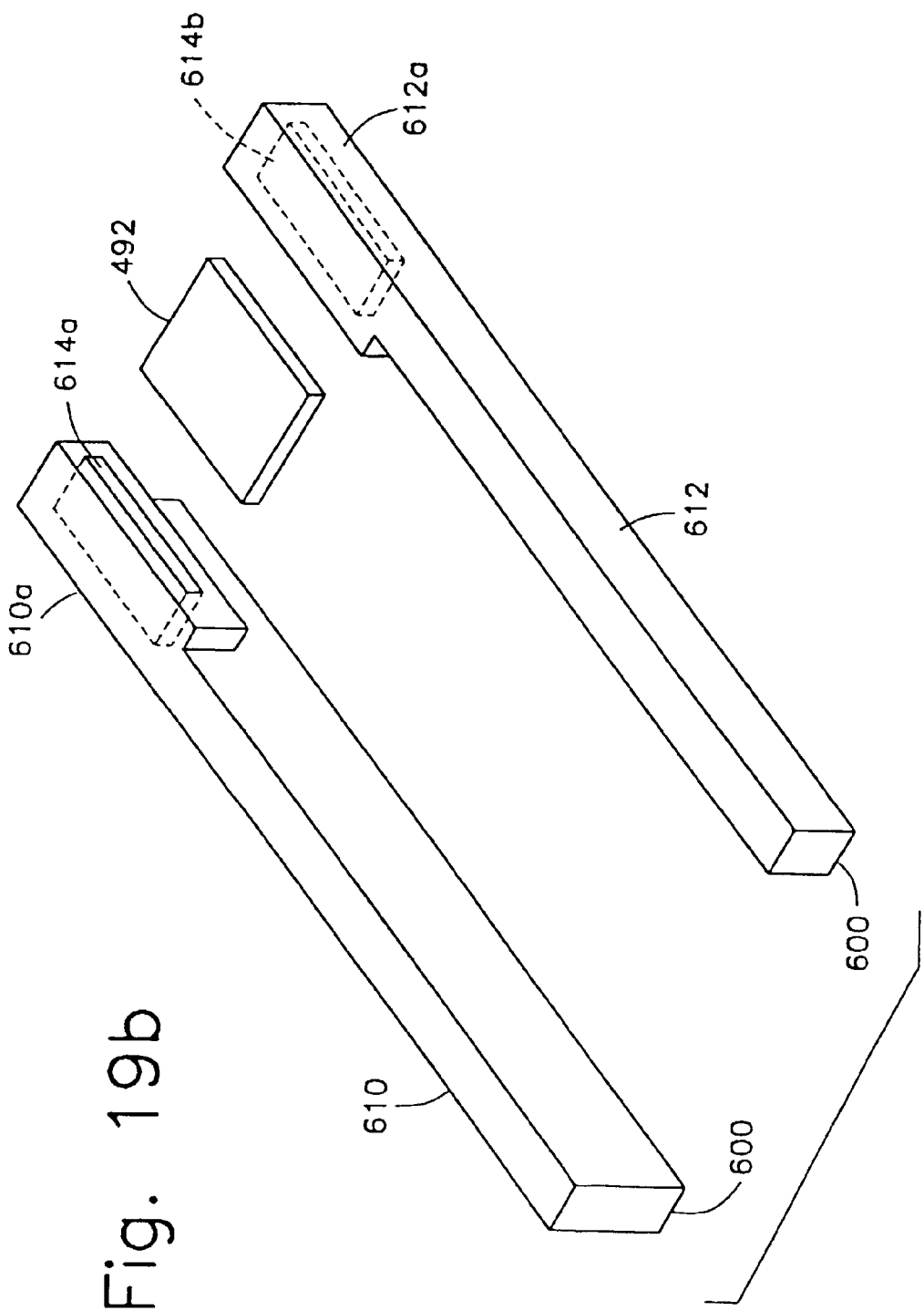

FIGS. 19a and 19b show a third alternative arrangement in which a pair of tissue blockers 600 and 602 facilitate the cutting of the resectioned tissue. Although, the following discussion will focus on the first tissue blocker 600, those skilled in the art will understand that a similar arrangement may be provided on the second tissue blocker 602.

As shown in FIG. 19a, the first tissue blocker 600 is composed of a first rectangular bar 610 and a second rectangular bar 612 situated at a first end 21a of the guiding slit 21. The first rectangular bar 610 has a first base 610a and the second rectangular bar 612 has a second base 612a, which are both fixedly coupled to the proximal face 14 of the anvil member 10 and arranged so that the bases 610a, 612b straddle both sides of the guiding slit 21 with a gap formed therebetween corresponding to the width of the guiding slit 21.

Figure 19C:
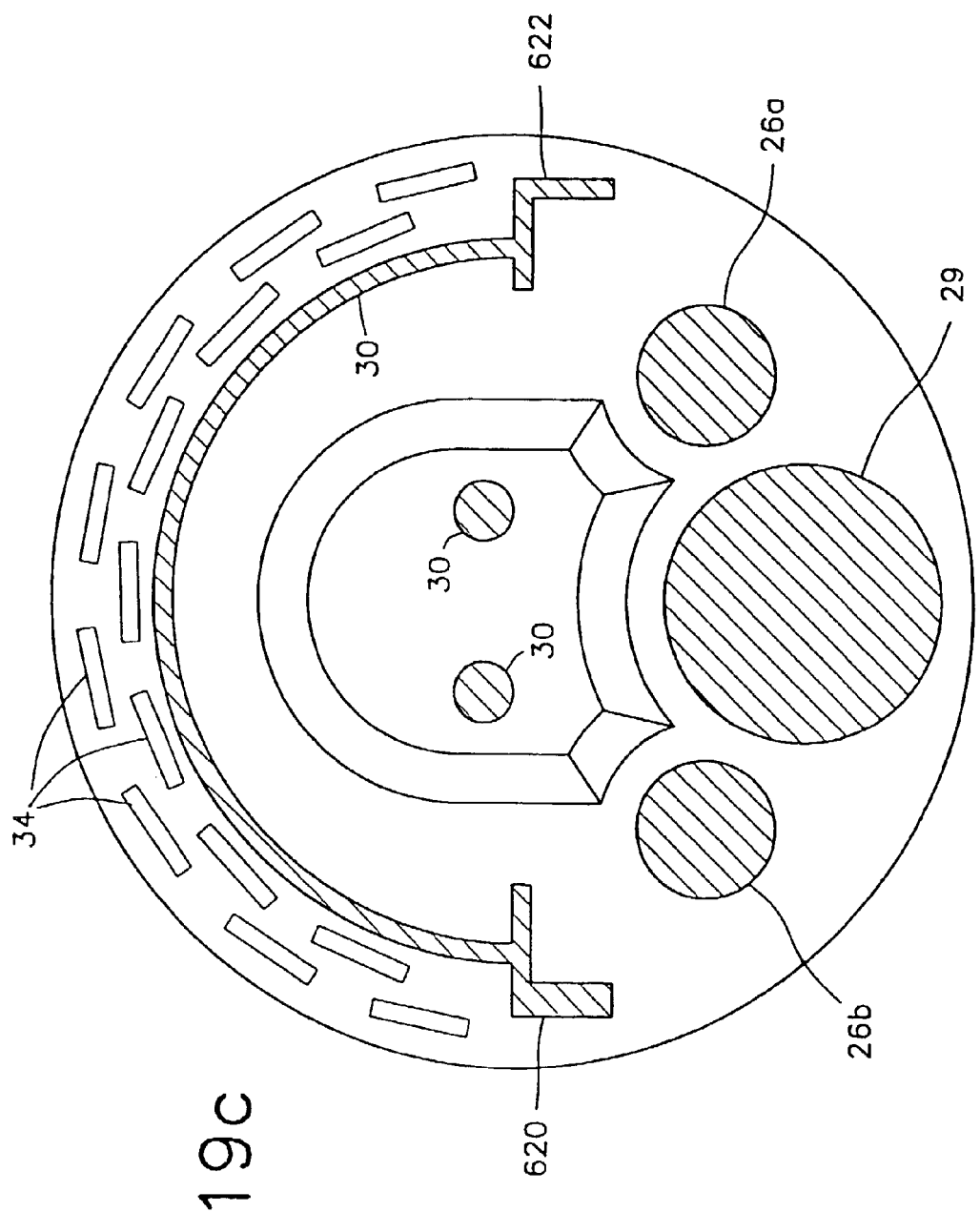

A first slot 614a is provided in the first base 610a of the first rectangular bar 610, and a second slot 614b is provided in the second base 612a of the second rectangular bar 612 so that when the rectangular bars 610, 612 are coupled to the anvil member 10, the flexible breakaway shield 482 (shown in FIG. 17) may be disposed within the slots 614a, 614b. As shown in FIG. 19c, a pair of L-shaped holes 620, 622 are provided on both ends of the blade slit 30 on the distal end 12a of the proximal housing 12. The L-shaped holes 620, 622 extend longitudinally within the proximal housing 12 to receive the rectangular bars 610, 612 therein when the anvil member 10 is coupled to the proximal housing 12.

This arrangement operates similarly to the arrangement shown in FIG. 17, so that the wiping action of the shield 482 in a direction opposite to a movement of the blade 202 allows the blade 202 to completely cut through the resectioned tissue. Although the shield 482 is initially a single piece in a first operation of the device, the shield 482 may be re-used without replacement in further operations with minimal diminishment of its effectiveness.

Figure 20:
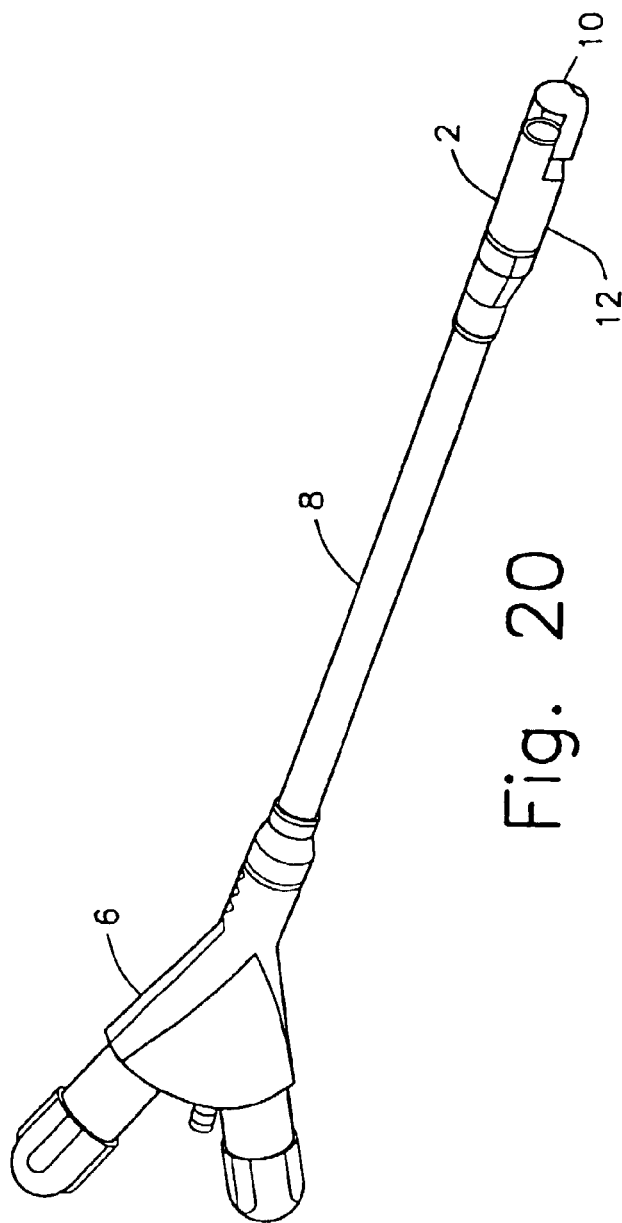
FIG. 20 shows a device according to a sixth embodiment of the present invention.

FIG. 20 shows a device according to a sixth embodiment of the present invention in which like reference numerals identify the same elements. The sheath 4 is substantially more rigid and shorter than in previous embodiments. Although this decreases the effective operative range of the device, the rigidity of the sheath 4 increases its overall structural strength, allowing greater forces to be transferred therethrough to the working head assembly 2 than in the previous embodiments. The cables 100, 450 driving the various mechanisms 102, 104 may then need to be stronger and stiffer in order to accommodate the increased forces. As a result of these changes, the overall size of the working head assembly 2 may then be increased to, for example, treat lesions that may be too large for the devices according to the previous embodiments to treat in a single procedure.

Figure 21:
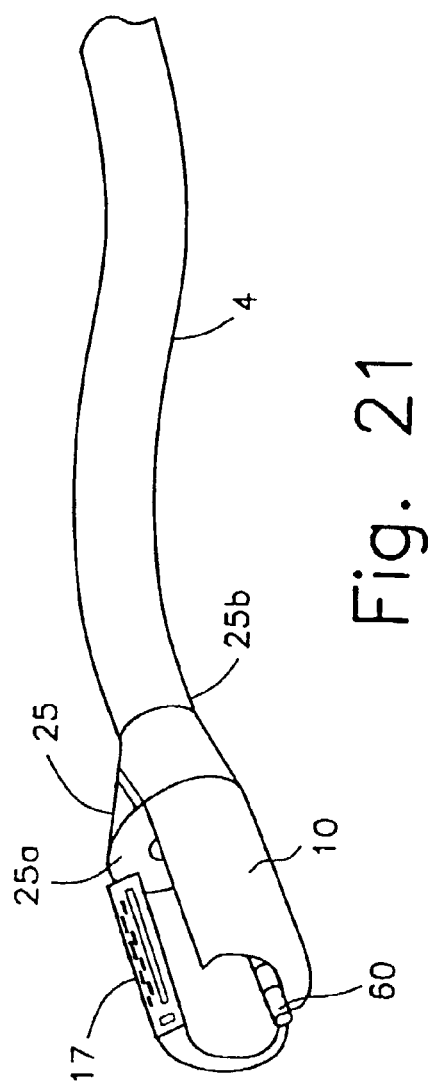
FIG. 21 shows a device according to a seventh embodiment of the present invention.
Figure 22:
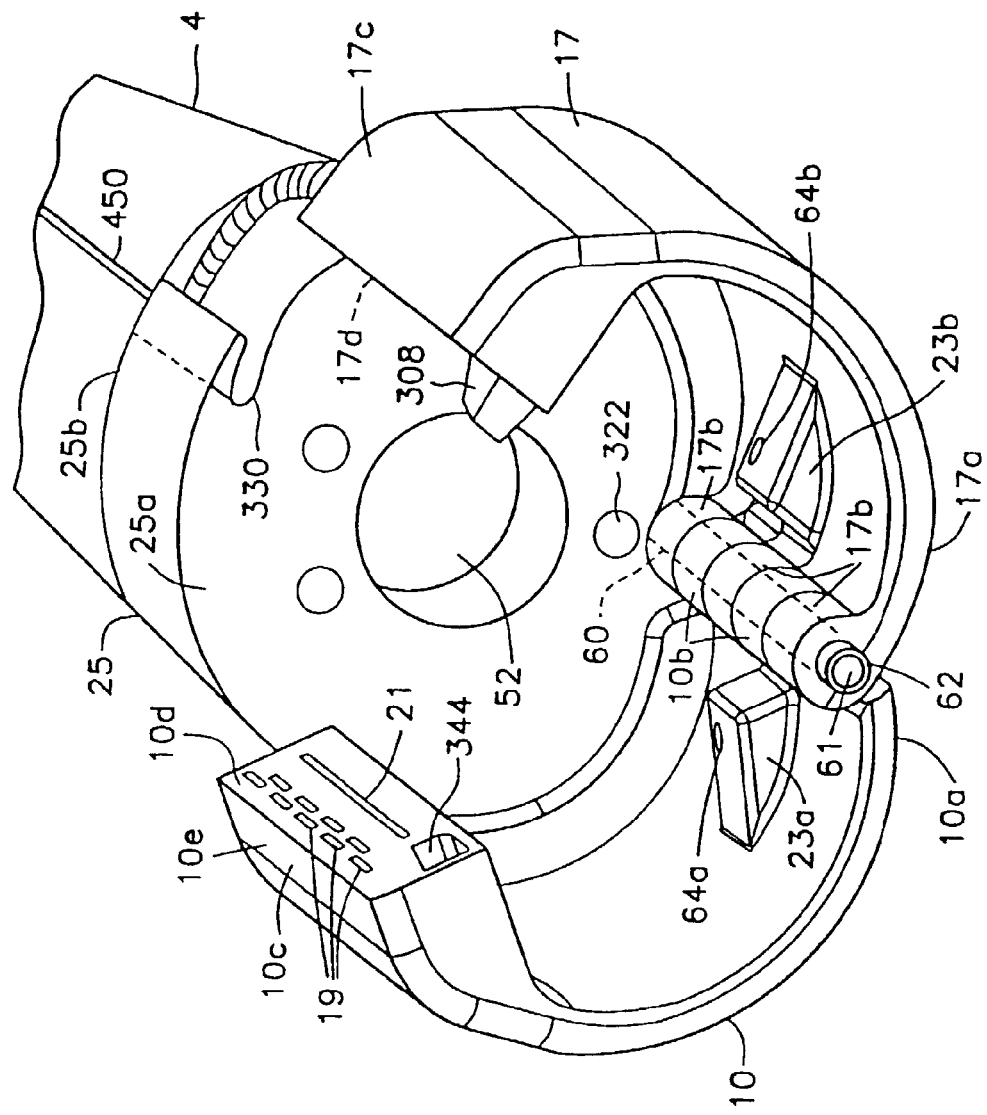
FIG. 22 shows a first perspective view of the device of FIG. 21.
Figure 23:
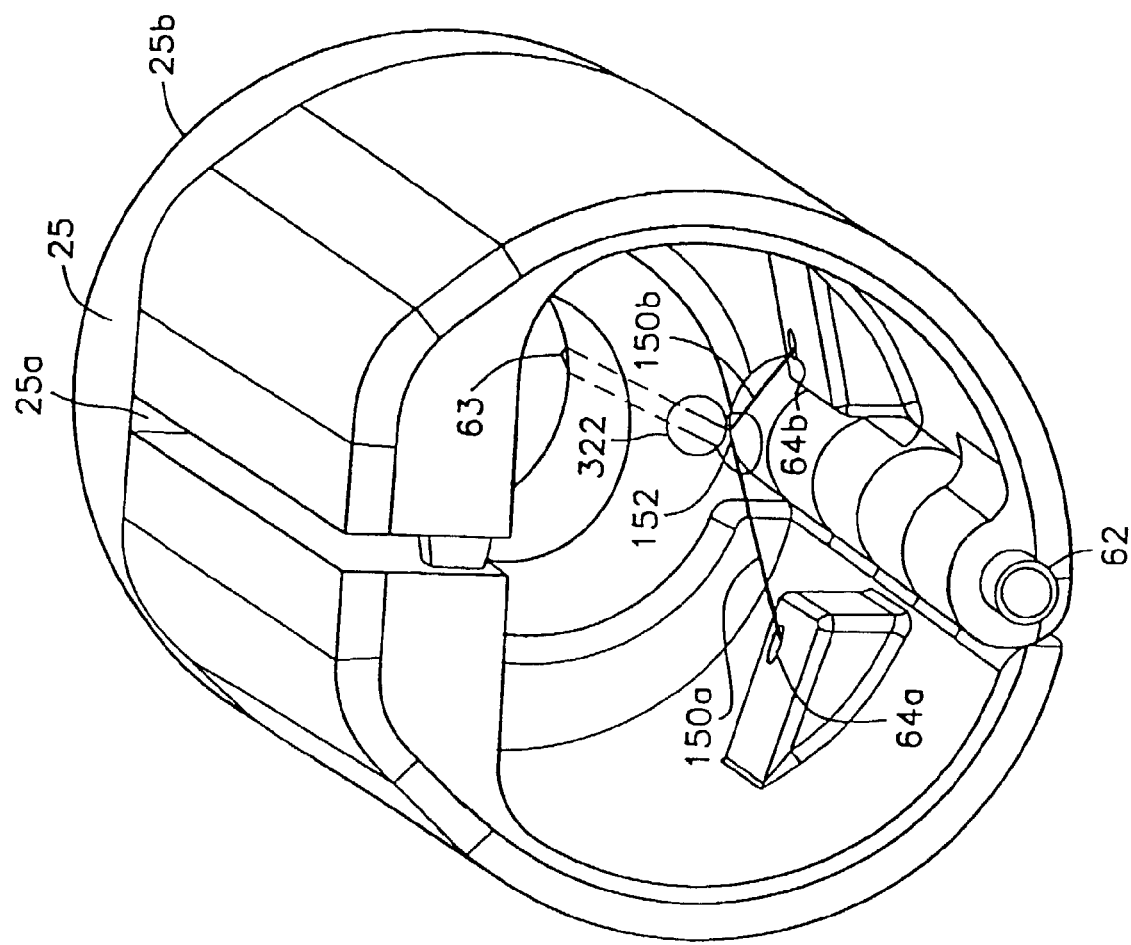
FIG. 23 shows a second perspective view of the device of FIG. 21.

FIGS. 21–25 show a device according to a seventh embodiment of the present invention in which the working head assembly 2 comprises the anvil member 10, a stapler member 17, and a connecting adapter 25. As shown in FIG. 21, the anvil member 10 and the stapler member 17 preferably have substantially semi-circular shapes complementary to one another such that, when they are positioned adjacent to each other, they form a 20. substantially annular clamp-like device (as shown in FIG. 23). The anvil member 10 and the stapler member 17 are pivotally connected via a substantially cylindrical hinge-pin 60 which is provided on a distal end 25a of the connecting adapter 25. A proximal end 25b of the connecting adapter 25 may preferably be coupled to the sheath 4 in a manner similar to that in which the proximal housing 12 is connected to the sheath 4 in the previous embodiments. Those skilled in the art will understand that the shape of the anvil member 10 and the stapler member 17 may be modified to accommodate specific needs or applications without departing from the scope of the present invention.

As shown in FIG. 22, a plurality of first ring-like extensions 10b are formed on a first end 10a of the anvil member 10. The first extensions 10b may preferably be separated a predetermined distance from one another to form a plurality of spaces in which a corresponding plurality of second ring-like extensions 17b formed on a first end 17a of the stapler member 17 are accommodated. The first extensions 10b may substantially correspond in shape and size to the second ring-like extensions 17b so that when the first anvil end 10a and the first stapler end 17a are engaged, an alternating arrangement of first and second extensions 10b, 17b is formed in which the holes of each of the first and second extensions lob, 17b are substantially aligned to form a continuous hole in which a hinge-pin 60 is received. Thus, the hinge-pin 60 and the first and second extensions 10b, 17b form a hinge which allows the anvil member 10 and the stapler member 17 to pivot about the hinge-pin 60. A locking ring 62 may preferably be attached to a distal end 61 of the hinge-pin 60 to secure the first and second extensions 10b, 17b to the hinge-pin 60.

A first anchoring joint 23a is formed on an interior face 10i of the anvil member 10. The first anchoring joint 23a may preferably have a substantially triangular cross-section viewed along the longitudinal axis of the working head assembly 2. However, a side of the first anchoring joint 23a that is attached to the anvil member 10 may preferably be convex in shape complementary to the concave shape of the interior face 10i of the anvil member 10. A substantially similar second anchoring joint 23b is formed on an interior face 17i of the stapler member 17 having a size and shape corresponding to the size and shape of the anchoring joint 23a.

As shown in FIG. 23, first and second coupling elements 64a, 64b are disposed on respective anchoring joints 23a, 23b to couple the anchoring joints 23a, 23b to two rod links 150a, 150b, respectively. The rod links 150a, 150b provide a rigid coupling between the anchoring joints 23a, 23b and a distal end 154 of a push rod 152. Thus, a longitudinal force in a distal or proximal direction applied to the push rod 152 is transferred to the anchoring joints 23a, 23b, and thereby to the anvil member 10 and the stapler member 17.

In operation, when a distally directed pushing force is applied to the push rod 152, the force is transferred through the link rods 150a, 150b to the anvil member 10 and the stapler member 17 via the respective anchoring joints 23a, 23b, gradually separating an anvil head 10c on the anvil member 10 from a stapler head 17c on the stapler member 17 until they reach a tissue receiving position. Similarly, when a proximally directed pulling force is applied to the push rod 152, the anvil head 10c and the stapler head 17c are drawn toward one another until they reach a stapling position, in which the anvil head 10c and the stapler head 17c are adjacent to one another separated by a narrow gap. As the anvil head 10c and the staler head 17c are drawn together by the push rod 152, a stabilizer tongue 308 extending from the stapler head 17c of the stapler member 17 is gradually received within a stabilizing groove 304 on the anvil head 10c. This tongue/groove arrangement provides a guide and a securing/stabilization mechanism for the anvil member 10 and the stapling member 17.

The anvil head 10c is disposed on a second end 10e of the anvil member 10 that is opposite to the first end 10a thereof. The anvil head 10c may preferably have a substantially rectangular cross-section larger than a cross-sectional size of the rest of the anvil member 10. The anvil head 10c has an anvil face 10d on which a plurality of staple-forming grooves 19 may preferably be arranged in two offset, substantially straight lines. In addition, a substantially straight guiding slit 21 may preferably extend substantially along the center of the anvil face 10d, substantially parallel to the lines of staple-forming grooves 19, while the stabilizing groove 304 is preferably formed along a distal side of the anvil face 10d for receiving the stabilizer tongue 308. The stabilizing groove 304 may preferably have a shape and size substantially corresponding to the stabilizing tongue 308 so that the stabilizing tongue 308 is snugly received within the stabilizing groove 304 when the anvil member 10 and the stapler member 17 are in the stapling position.

Figure 23A:
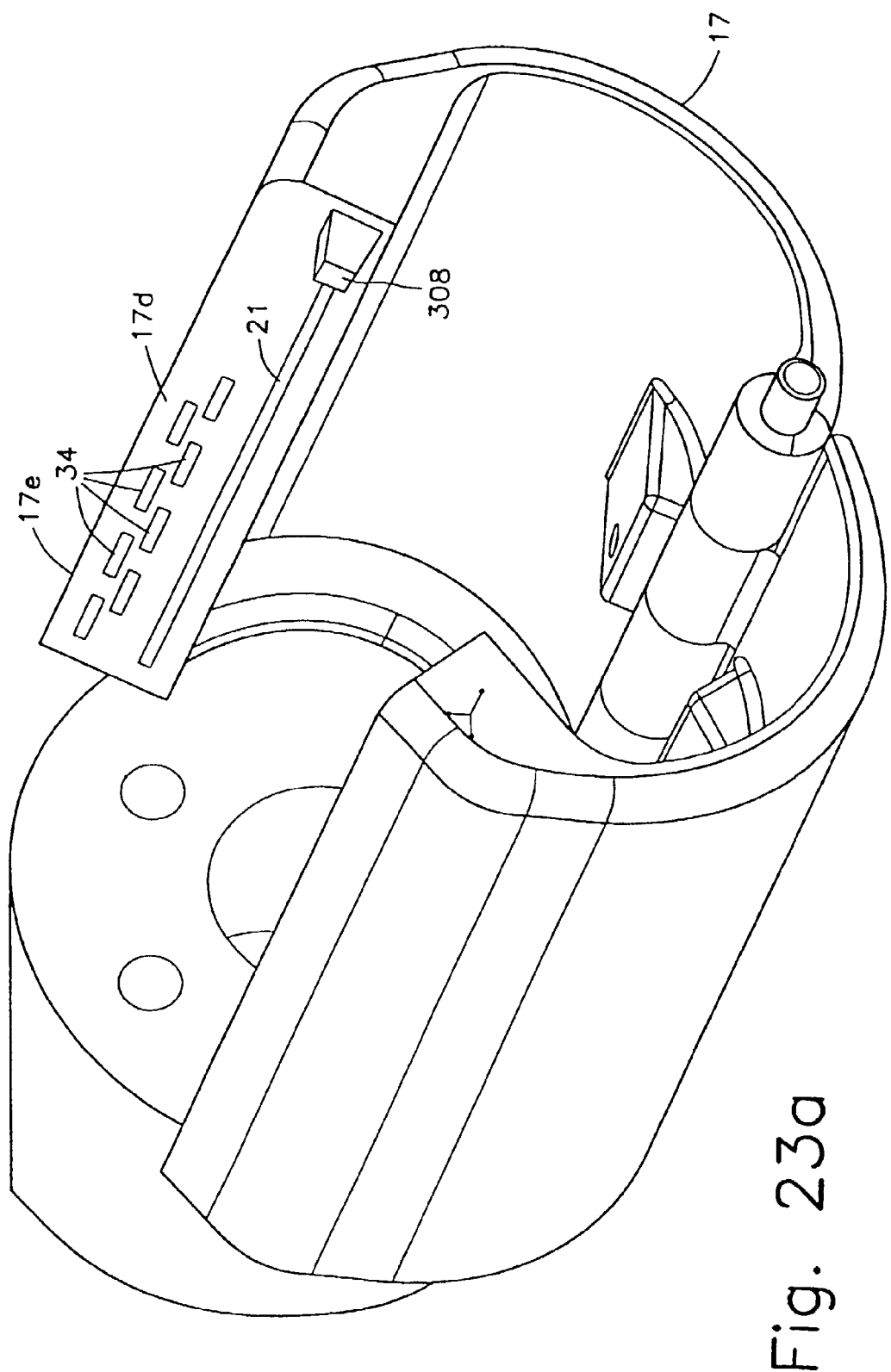
FIG. 23a shows a third perspective view of the device of FIG. 21.

As shown in FIG. 23a, the stapler head 17c is formed on a second end 17e of the stapler member 17 opposite to the first end 17a thereof, and preferably has a cross-section corresponding, at least in the area adjacent to a stapler face 17d, to the size and shape of the anvil head 10c. A plurality of staple slits 34 are arranged on the stapler face 17d in positions corresponding to the position of the staple-forming grooves 19 on the anvil head 10c so that when the stapler face 17d and anvil face 10d are positioned adjacent to each other, each of the plurality of staple slits 34 is substantially aligned with a corresponding one of the plurality of staple-forming groove 19. Additionally, a substantially straight blade slit 36 extends across the stapler face 17d corresponding to the guiding slit 21 on the anvil head 10c so that when the stapler head 17c and the anvil head 10c are positioned adjacent to one another, the blade slit 36 is substantially aligned with the guiding slit 21.

Figure 24:
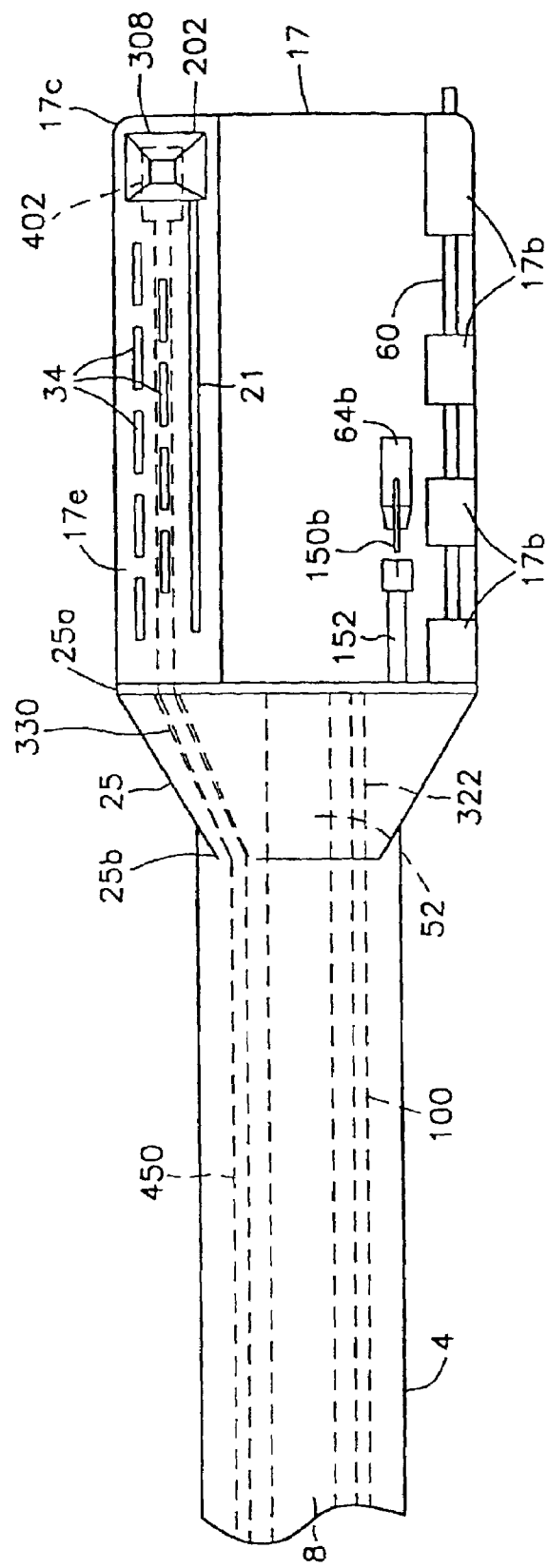
FIG. 24 shows a side cut-away view of the device of FIG. 21.

As shown in FIG. 23, the distal end 25a of the connecting adapter 25 preferably has a cross-section corresponding to the shape and size of the peripheral surface of the annular clamp-like shape formed by the anvil member 10 and the stapler member 17 so that a substantially smooth, continuous outer surface is formed by the anvil member 10, the stapler member 17, and the connecting adapter 25 when the anvil member 10 and the stapler member 17 are in the stapling position. The connecting adapter 25 is preferably gradually tapered from the distal end 25a to the proximal end 25b thereof, and the proximal end 25b may then be coupled to the sheath 4 as shown in FIG. 24. As further shown in FIG. 24, a substantially cylindrical endoscope lumen 52 preferably extends axially through the center of the connecting adapter 25 for receiving a conventional endoscope 8 therethrough. The connecting adapter 25 may also have a substantially cylindrical rod hole 322 extending axially along the periphery of the connecting adapter 25 extending through an area adjacent to the hinge-pin 60, for receiving the push rod 152 therein.

Figure 25:
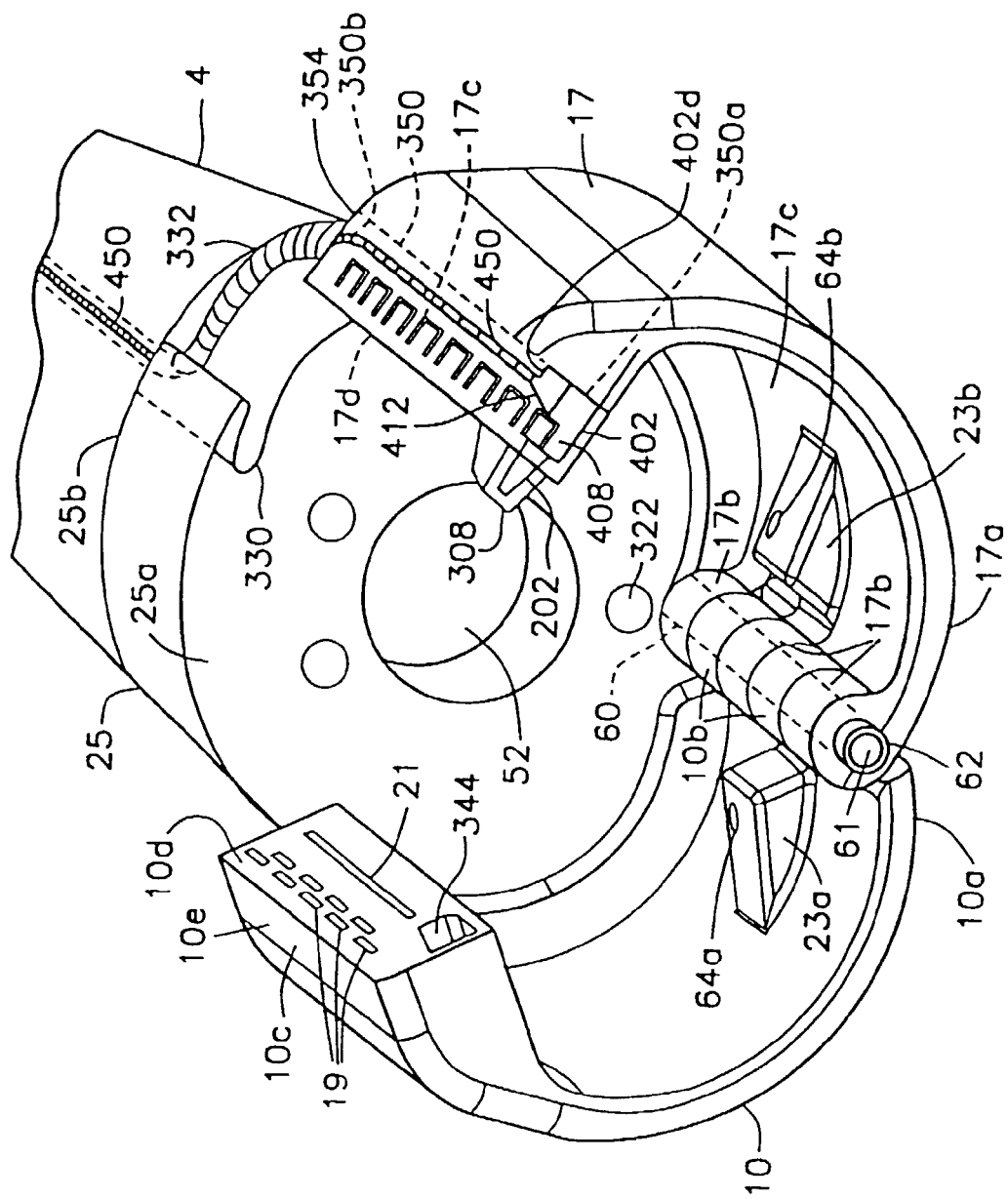
FIG. 25 shows a fourth perspective view of the device of FIG. 21.
Figure 26:
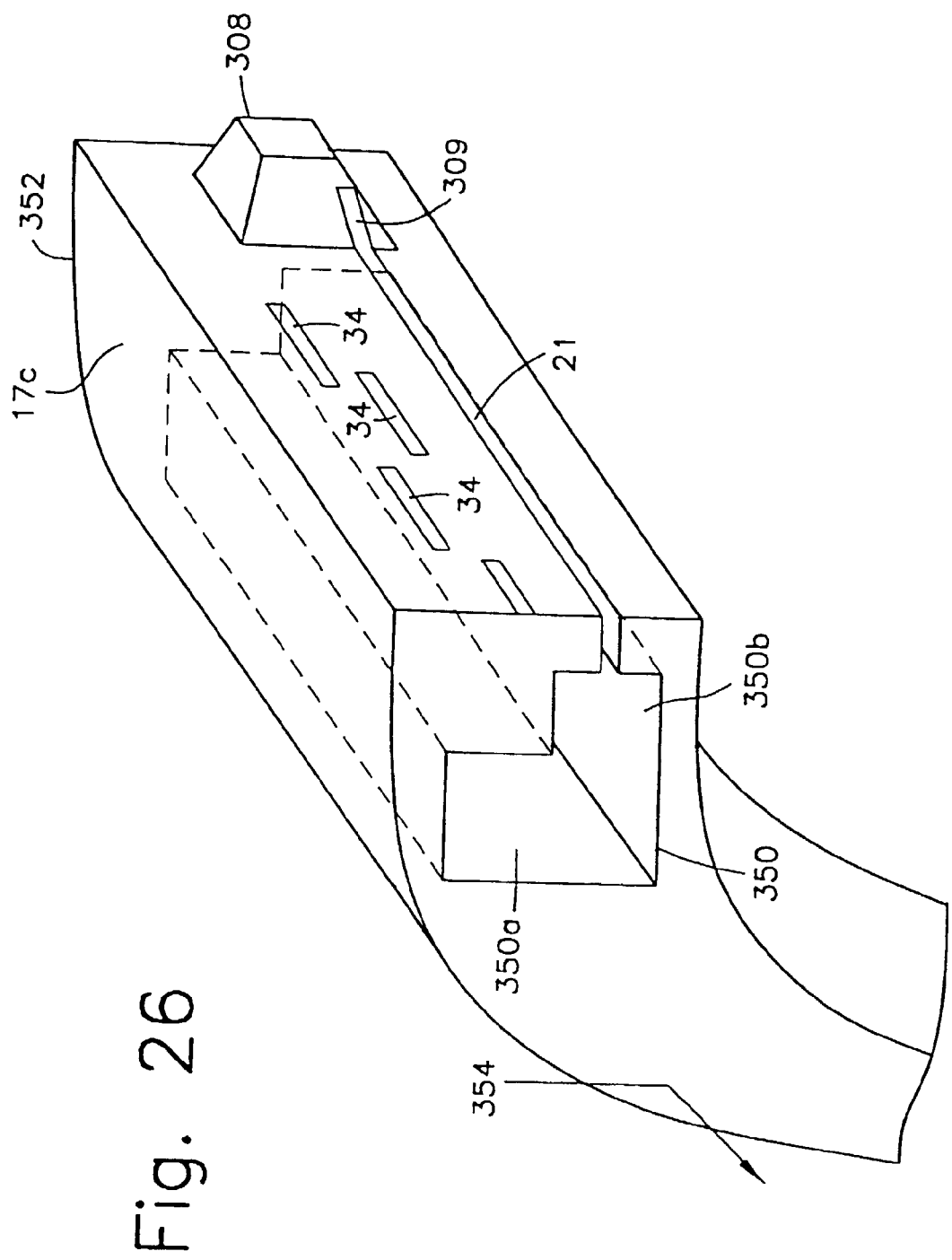
FIG. 26 shows a cut-away view of an exemplary stapler member of the device of FIG. 1.

As shown in the cut-away view of FIG. 25, a track 350 is provided within the stapler head 17c extending within the stapler head 17c from an area adjacent to a distal end 352 of the stapler head 17c to an area adjacent to a proximal end 354 thereof. FIG. 26 shows a cutaway view of the stapler head 17c showing the track 350 having a substantially L-shaped cross-section. The track 350 may preferably be situated so that a first leg 350a of the track 350 extends substantially beneath the plurality of staple slits 34 on the staple face 17d, and a second leg 350b of the track 350 extends substantially beneath the blade slit 21 on the staple face 17d.

In a first configuration shown in FIG. 25, a wedge-sled 402 is provided (instead of the wedge 402 described in the previous embodiments) on a distal end 350a of the track 350. The wedge-sled 402 has a cut-out in a corner forming a cam surface 412 thereon and a blade handle 408. This provides the wedge-sled 402 with a substantially L-shaped cross-section substantially corresponding to the cross-sectional shape of the track 350. The wedge-sled 402 is arranged in the track 350 so that the cam surface 412 is substantially disposed in the first leg 350a of the track facing toward the plurality of staple slits 34. Furthermore, the wedge-sled 402 is arranged in the track 350 so that the blade handle 408 is subsantially disposed in the second leg 350b beneath the blade slit 21. Thus, when the cutting blade 202 is coupled to the blade handle 408, the cutting blade 202 extends out of the blade slit 21 as in the previous embodiments. As shown in FIG. 26, the stabilizing tongue 308 has a receiving slit 309 for receiving the cutting blade 202 therein when the wedge-sled 402 is positioned at the distal end 350a of the track 350. This prevents unintentional cutting of tissue as the device is inserted and guided within the organ.

As shown in FIG. 25, an actuating cable 450 for operating the stapler head 17c is coupled to the leading edge 402d of the wedge-sled 402 and extends through the track 350, through a tube 332 (which is coupled to the proximal end 354 of the stapler head 17c and extends through the sheath 4 to the control handle) of the plurality of tubes 510 (shown in FIG. 9d), and is then coupled to the control handle 6 (not shown).

In operation, the wedge-sled 402 is initially positioned at the distal end 350a of the track 350 with the blade 202 received within the receiving slit 309 of the stabilizing tongue 308 as the operator maneuvers the device to a desired location within the body. While the device is being maneuvered to the desired location, the anvil member 10 and the stapler member 17 are located adjacent to each other in the stapling position. When the desired position is reached, the operator pushes the push rod 152 distally to separate the anvil member 10 and the stapler member 17 into the tissue receiving position. Then the operator draws the portion of tissue to be resectioned into the gap between the stapler member 17 and the anvil member 10 and draws the push rod 152 proximally to return the anvil member 10 and the stapler member 17 to the stapling position, gripping the tissue to be resected within the gap. The operator then pulls actuating cable 450 proximally, drawing the wedge-sled 402 towards the proximal end 350b of the track 350. As the cam surface 412 on the wedge-sled passes beneath each one of the plurality of staple slits 34, the cam surface 412 drives each one of a plurality of staple drivers 472 (each being disposed within a corresponding one of the staple slits 34) sequentially driving a plurality of staples out of the staple slits 34 to staple the tissue gripped between the anvil head 10c and the stapler head 17c. In addition, the cutting blade 202 coupled to the blade handle 408 of the wedge-sled 402 is pulled through the blade slit 21 to resection the tissue which has now been stapled off from the organ.

When the tissue has been resectioned, the operator pushes the operating cable 450 distally to return the cutting blade 202 to the receiving slit 309 of the stabilizing wedge 308. The device may then be withdrawn from the body.

As shown in FIGS. 23 and 25, the anvil member 10 and the stapler member 17 have a tissue receiving position shown in FIG. 25, and a stapling position shown in FIG. 23. Therefore, it is necessary to allow the actuating cable 450 disposed within the tube 332 and received within the stapler head 17c to correspondingly move with the stapler member 17. Accordingly, a channel 330 is provided in the connecting adapter 25 to receive the tube 332 therein. The channel 330 may preferably be formed within the connecting adapter 25 to substantially correspond to the arc path along which the tube 332 is pulled by the stapler member 17, as the stapler member 17 moves between the tissue receiving and the stapling positions. Thus, the channel minimizes bending and crimping of the tube 332.

Those skilled in the art will understand that although the proximal housing 12 in any of the embodiments may preferably be composed of a metallic-type material, the proximal housing 12 may also be composed of a clear plastic-type material which would allow the user to operate the working head assembly 2 under visual observation by partially withdrawing the endoscope 8 into the second endoscope lumen 52 in the proximal housing 12. The user could then look through the walls of the endoscope lumen 52 into the proximal housing 12 to, for example, observe whether each of the plurality of staple drivers 472 have been actuated. In addition, the user may also observe whether the wedge 402 shown in FIGS. 10a and 10b is locked into the blade portion 420 as described above. Alternatively, selected portions of the proximal housing 12 may be composed of the clear plastic-type material providing a "window" to view through the proximal housing 12.

Those skilled in the art will also understand that although the above-described embodiments show mechanical force transmission between the control handle and the working head assembly, this device could alternatively include an electronic control for receiving input from an operator coupled to a series of motors in the working head assembly. Those skilled in the art will further understand that the relative positioning of the stapling mechanisms and the position adjusting mechanisms to each other may be reversed, placing the stapling mechanisms in a distal-most position in relation to the position adjusting mechanism. The above described embodiments are for purposes of illustration only and the various modifications of these embodiments which will be apparent are considered to be within the scope of the teachings of this invention which is to be limited only by the claims appended hereto.

What is claimed is:

1. A method of performing a full-thickness resection within a body organ, comprising the steps of:
   slidably coupling a stapling head to a flexible endoscope;
   inserting the stapling head into a body lumen via a naturally occurring body orifice and sliding the stapling head along the endoscope to a desired location within the body lumen;
   drawing a folded full-thickness portion of tissue to be resected between a stapling mechanism and an anvil of the stapling head so that two full thicknesses of the lumenal tissue are located between the anvil and the stapling mechanism;
   firing a plurality of staples through the folded portion of tissue to couple together the fold; and
   cutting away from the lumen wall a portion of tissue radially within the staples so that the body lumen remains sealed by the staples.

* * * * *

UNITED STATES PATENT AND TRADEMARK OFFICE
CERTIFICATE OF CORRECTION

PATENT NO. : 7,059,331 B2
APPLICATION NO. : 10/251192
DATED : June 13, 2006
INVENTOR(S) : Adams et al.

Page 1 of 1

It is certified that error appears in the above-identified patent and that said Letters Patent is hereby corrected as shown below:

On the Title Page, Item (63) Related U.S. Application Data section should be replaced with the following:

This application is a Divisional of prior U.S. Patent Application Serial No. 10/055,306 filed Jan. 23, 2002 now U.S. Patent No. 6,478,210 entitled "Method and Device for Full Thickness Resectioning of an Organ" which is a Continuation of U.S. Patent Appln. Serial No. 09/813,944 filed Mar. 22, 2001 now U.S. Patent No. 6,343,731 entitled "Method and Device for Full Thickness Resectioning of an Organ" which is a Continuation of U.S. Patent Appln. Serial No. 09/694,894 filed Oct. 25, 2000 now U.S. Patent No, 6,241,140 entitled "Method and Device for Full Thickness Resectioning of an Organ" which is a Continuation of U.S. Patent Appln. Serial No. 09/316,674 filed May 21, 1999 now U.S. Patent No. 6,179,195 entitled "Method and Device for Full Thickness Resectioning of an Organ" which is a Divisional of U.S. Patent Appln. Serial No. 09/100,393 filed June 19, 1998 now U.S. Patent No. 6,126,058 entitled "Method and Device for Full Thickness Resectioning of an Organ." All applications are expressly incorporated herein, in their entirety, by reference.

Signed and Sealed this

Twenty-third Day of March, 2010

David J. Kappos
*Director of the United States Patent and Trademark Office*